United States Patent
Ye et al.

(10) Patent No.: US 11,143,024 B2
(45) Date of Patent: Oct. 12, 2021

(54) APPLICATION OF ELECTROCHEMICAL IMPEDANCE SPECTROSCOPY FOR ANALYZING SAG OF DRILLING FLUIDS

(71) Applicant: Halliburton Energy Services, Inc., Houston, TX (US)

(72) Inventors: Xiangnan Ye, Cypress, TX (US); Dale E. Jamison, Humble, TX (US); Li Gao, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 119 days.

(21) Appl. No.: 16/606,361

(22) PCT Filed: Dec. 21, 2017

(86) PCT No.: PCT/US2017/067958
§ 371 (c)(1),
(2) Date: Oct. 18, 2019

(87) PCT Pub. No.: WO2019/125472
PCT Pub. Date: Jun. 27, 2019

(65) Prior Publication Data
US 2021/0062647 A1    Mar. 4, 2021

(51) Int. Cl.
*E21B 49/00* (2006.01)
*E21B 47/113* (2012.01)
(Continued)

(52) U.S. Cl.
CPC .......... *E21B 49/005* (2013.01); *E21B 47/113* (2020.05); *E21B 47/18* (2013.01); *G01N 27/026* (2013.01); *G01N 33/2823* (2013.01)

(58) Field of Classification Search
CPC ............................ E21B 49/005; G01N 27/026
See application file for complete search history.

(56) References Cited

U.S. PATENT DOCUMENTS 6,176,323 B1 * 1/2001 Weirich ................. E21B 21/08
175/40
6,330,826 B1   12/2001 Meeten
(Continued)

FOREIGN PATENT DOCUMENTS

WO      2018038717        3/2018

OTHER PUBLICATIONS

Kulkarni et al. "Modeling Real-Time Sag in the Wellbore," SPE-178832 (Year: 2016).*
(Continued)

*Primary Examiner* — John Fitzgerald
(74) *Attorney, Agent, or Firm* — Tenley Krueger; C. Tumey Law Group PLLC

(57) ABSTRACT

Systems and methods for determining the composition of a drilling fluid using electro-rheology may be provided. A method for drilling a wellbore may include: circulating a drilling fluid in a wellbore; extending the wellbore into one or more subterranean formations; measuring impedance of at least a portion of the drilling fluid over time as one or more particulate additives in the drilling fluid settle; determining one or more model elements of an equivalent circuit model for modeling frequency responses of the drilling fluid from the impedance; and determining sag behavior of the drilling fluid based, at least partially, on the one or more model elements.

20 Claims, 12 Drawing Sheets

(51) Int. Cl.
  *E21B 47/18* (2012.01)
  *G01N 27/02* (2006.01)
  *G01N 33/28* (2006.01)

(56) References Cited

U.S. PATENT DOCUMENTS

| | | | |
|---|---|---|---|
| 7,078,910 B2* | 7/2006 | Hirthe | G01N 33/2888 |
| | | | 324/446 |
| 7,088,115 B1* | 8/2006 | Glenn | G01N 27/026 |
| | | | 324/691 |
| 7,199,595 B2* | 4/2007 | Wooton | G01N 33/2888 |
| | | | 324/698 |
| 10,202,843 B2* | 2/2019 | Wroblewski | G01N 29/028 |
| 2005/0184734 A1* | 8/2005 | Sosnowski | G01N 27/026 |
| | | | 324/444 |
| 2006/0214671 A1 | 9/2006 | Wooton et al. | |
| 2012/0013335 A1 | 1/2012 | Saasen et al. | |
| 2014/0060819 A1* | 3/2014 | Pindiprolu | E21B 33/14 |
| | | | 166/250.01 |
| 2014/0172305 A1* | 6/2014 | Jamison | E21B 44/00 |
| | | | 702/9 |
| 2014/0182363 A1* | 7/2014 | Potyrailo | G01N 27/026 |
| | | | 73/64.53 |
| 2014/0202772 A1* | 7/2014 | Kulkarni | E21B 21/08 |
| | | | 175/65 |
| 2014/0209393 A1* | 7/2014 | Jamison | E21B 43/267 |
| | | | 175/217 |
| 2015/0211350 A1* | 7/2015 | Norman | E21B 21/00 |
| | | | 700/275 |
| 2015/0354343 A1 | 12/2015 | Wroblewski et al. | |
| 2016/0369627 A1* | 12/2016 | Kulkarni | E21B 21/08 |
| 2017/0051606 A1 | 2/2017 | Fanini et al. | |
| 2019/0227048 A1* | 7/2019 | Ye | G01N 33/2823 |
| 2019/0309613 A1* | 10/2019 | Jamison | E21B 44/00 |
| 2019/0360286 A1* | 11/2019 | Ye | E21B 49/087 |
| 2020/0308964 A1* | 10/2020 | Ye | G01R 27/16 |
| 2020/0378252 A1* | 12/2020 | Ye | G01N 31/164 |

OTHER PUBLICATIONS

ISRWO International Search Report and Written Opinion for PCT/US2017/067958 dated Jul. 4, 2019.

Omland, T. H., Saasen, A., Taugbol, K., Jorgensen, T., Reinholt, F., Amundsen, P. A., . . . Steele, A. (2007). Improved Drilling Process Control Through Continuous Particle and Cuttings Monitoring. Digital Energy Conference and Exhibition.

Dewhurst, R. J. (2012). Measurement Science and Technology: a historical perspective. Measurement Science and Technology, 24(1), 012006.

* cited by examiner

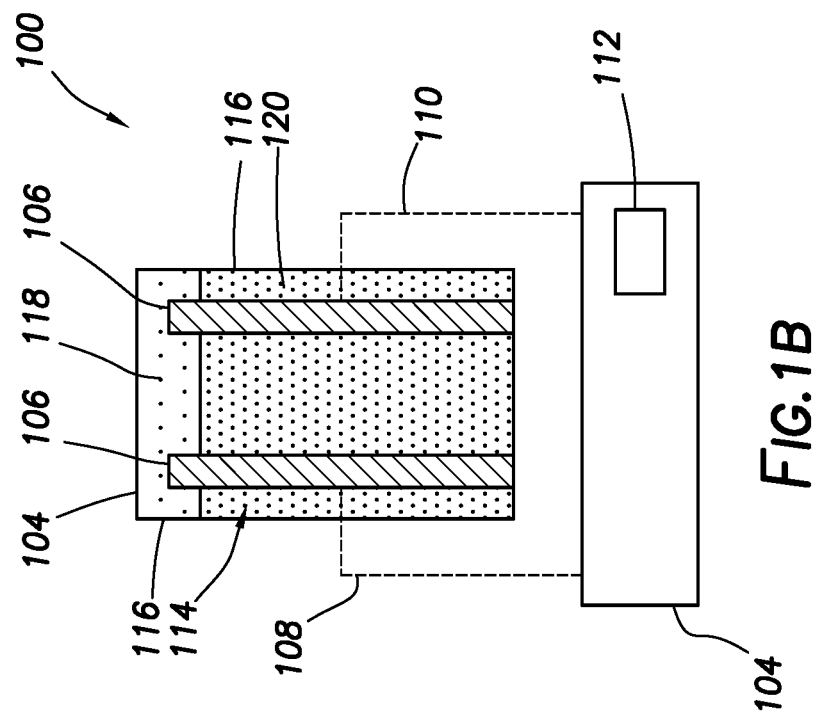
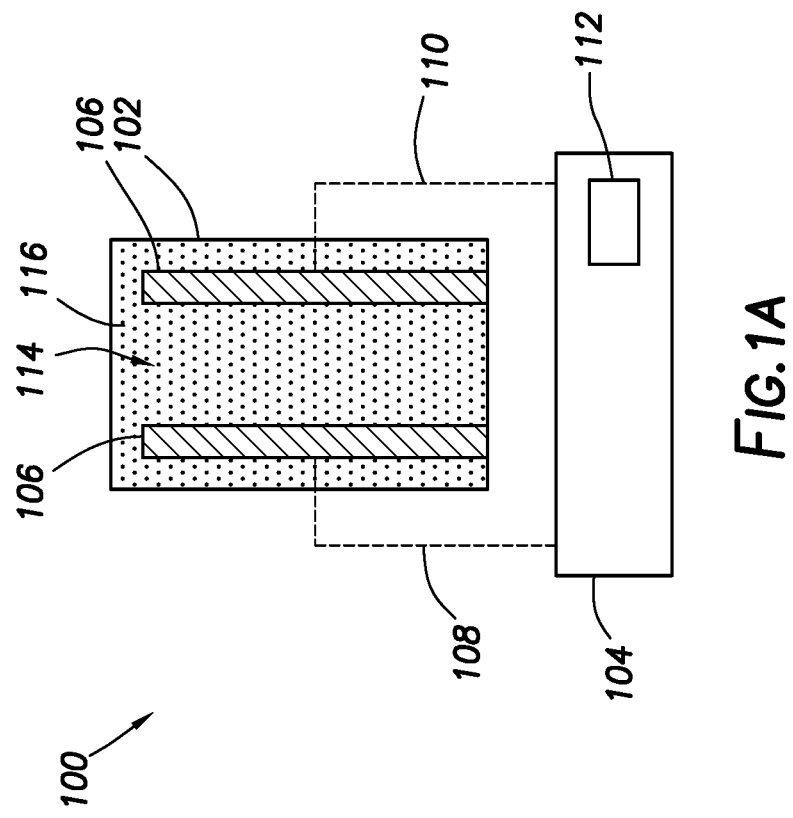

APPLICATION OF ELECTROCHEMICAL IMPEDANCE SPECTROSCOPY FOR ANALYZING SAG OF DRILLING FLUIDS

BACKGROUND

During the drilling of a wellbore into a subterranean formation, a drilling fluid, also referred to as a drilling mud, may be continuously circulated from the well surface down to the bottom of the wellbore being drilled and back to the well surface again. The drilling fluid may include a mixture of water, oil, additives (e.g., viscosifiers, weighting materials, emulsifying surfactants, and the like), and combinations thereof, to impart certain properties to the drilling fluid to satisfy different drilling requirements.

The drilling fluid can serve several functions, one of them being to transport wellbore cuttings up to the surface where they are separated from the drilling fluid. Another function of the drilling fluid can include providing hydrostatic pressure against the wall of the drilled wellbore, thereby preventing wellbore collapse and the resulting influx of gas or liquid from the formations being penetrated. The density of the drilling fluid may be maintained, for example, to control the hydrostatic pressure that the drilling exerts at the bottom of the wellbore.

In the most common applications, the density of the drilling mud may be increased by adding particulate weighting agents, such as barite and hematite. These particles may be prone to sedimentation within the drilling fluid under the influence of gravity. The sedimentation of these and other particulates in the drilling fluid is referred to as "sag." Sag can occur, for example, when circulation of the drilling fluid is stopped for a period of time, e.g., when the drill string must be tripped from the well, and is caused by the resulting sedimentation or stratification of the drilling whereby "heavy spots" and "light spots" develop. Sag can also involve movement or shifting of these heavy and light fractions, particularly the "heavy spots", where components such as the weighting agent have become concentrated. Sag may not occur throughout an entire well, but its occurrence in even a small section of the well may be problematic. For instance, sag in a drilling fluid can cause density variations in the wellbore, potentially causing the drilling fluid to provide inadequate hydrostatic pressure. Sag of the weighting agents in a fluid used in oil field operations can cause large density variations that often lead to significant wellbore pressure management problems and potentially, wellbore failure. Additionally, sag may also lead to sticking of drill pipe, difficulty in re-initiating and/or maintaining proper circulation of the fluid, possible loss of circulation and disproportionate removal from the well of lighter components of the fluid.

Different techniques have been used to determine the sag of a drilling fluid in both laboratory and field. These include static sag testing, dynamic flow-loops, viscometer sag testing, indirect measurement using ultrasonic and Nuclear Magnetic Resonance, and direct measurements, among others. The most common method is the static sag testing recommended by the American Petroleum Institute in API Recommended Practice 13B-2: Recommended Practice for Field Testing Oil-Based Drilling Fluids. However, the API Recommended Practice is typically considered a time consuming process that can lead to erroneous results, for example, due systematic and human errors during measurement.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

FIGS. 1A and 1B illustrate an embodiment of an EIS fluid analysis system having a pair of parallel plates in a vertical configuration.

DETAILED DESCRIPTION

Figure 2:
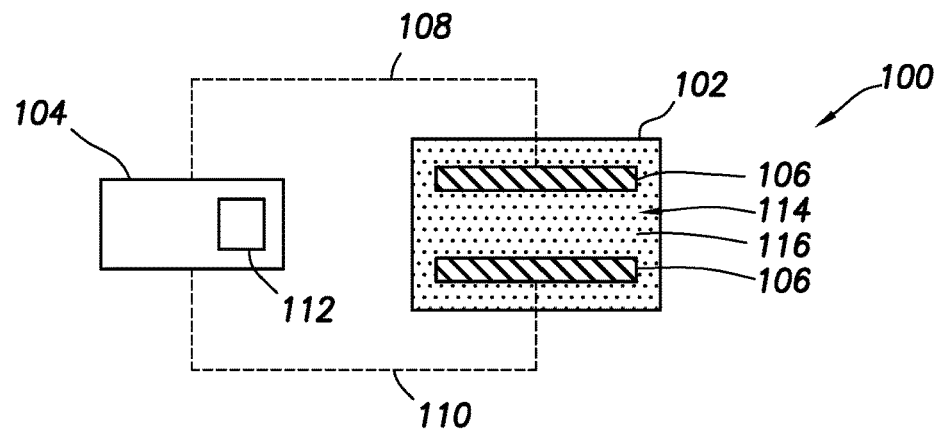
FIG. 2 illustrates an embodiment of an EIS fluid analysis system having a pair of parallel plates in a horizontal configuration.

The present disclosure relates to drilling operations and, more particularly, embodiments disclosed herein are directed to systems and methods that use electrochemical impedance spectroscopy (EIS) for analyzing sag behavior of drilling fluids. As will be discussed in more detail below, correlations may be developed using EIS that can then be used to characterize the sag of drilling fluids. For example, the sag may be characterized by monitoring the change of impedance over time. The systems and methods may be used to monitor the sag behavior of drilling fluid in a mud pit, on a rig, in a mud plant, in a laboratory, or at any other suitable location. EIS is a non-invasive technique for measuring properties of a medium as a function of frequency (also referred to as the excitation frequency). Although the systems and methods described herein with reference to sag of drilling fluids, the sag of other fluid types may also be determined using the presently described system and methods.

The drilling fluid may include hydrocarbon-based drilling fluids, which may include a hydrocarbon liquid as the base fluid. The hydrocarbon may be synthetic or oil-based. In addition, the techniques may also be extended to water-based drilling fluids. The drilling fluid may include invert emulsion, which may include an external phase and an internal phase. The external phase may comprise a hydrocarbon liquid. The external phase may include a hydrocarbon liquid. The external phase can include dissolved materials or undissolved solids. Any suitable hydrocarbon liquid may be used in the external phase, including, but not limited to, a fractional distillate of crude oil; a fatty derivative of an acid, an ester, an ether, an alcohol, an amine, an amide, or an imide; a saturated hydrocarbon; an unsaturated hydrocarbon; a branched hydrocarbon; a cyclic hydrocarbon; and any combination thereof. Crude oil can be separated into fractional distillates based on the boiling point of the fractions in the crude oil. An example of a suitable fractional distillate of crude oil is diesel oil. The saturated hydrocarbon can be an alkane or paraffin. For example, the saturated hydrocarbon may be an isoalkane, a linear alkane, or a cyclic alkane. Examples of suitable saturated hydrocarbons may include a combination of an isoalkane and an n-alkane or a mineral oil blend that includes alkanes and cyclic alkanes. The unsaturated hydrocarbon may include an alkene, alkyne, or aromatic. The alkene may include an isoalkene, linear alkene, or cyclic alkene. The linear alkene may include a linear alpha olefin or an internal olefin. The hydrocarbon liquid may be present in the drilling fluid in an any suitable amount, including an amount ranging from about 1 wt. % to about 90 wt. % based on a total weight of the drilling fluid. For example, the hydrocarbon liquid may be present in the drilling fluid in an amount of about 10 wt. %, about 20 wt. %, about 30 wt. %, about 40 wt. %, about 50 wt. %, about 60 wt. %, about 70 wt. %, about 80 wt. %, or about 90 wt. %, based on a total weight of the drilling fluid. One of ordinary skill in the art with the benefit of this disclosure should recognize the appropriate amount of the aqueous liquid for a chosen application.

The internal phase may include an aqueous liquid. The aqueous liquid may be from any source provided that it does not contain an excess of compounds that may undesirably affect other components in the drilling fluids. For example, a drilling fluid may include fresh water or salt water. Salt water generally may include one or more dissolved salts therein and may be saturated or unsaturated as desired for a particular application. Seawater or brines may be suitable for use in some examples. The aqueous liquid may be present in the drilling fluid in an any suitable amount, including an amount ranging from about 1 wt. % to about 90 wt. % based on a total weight of the drilling fluid. For example, the aqueous liquid may be present in the drilling fluid in an amount of about 10 wt. %, about 20 wt. %, about 30 wt. %, about 40 wt. %, about 50 wt. %, about 60 wt. %, about 70 wt. %, about 80 wt. %, or about 90 wt. %, based on a total weight of the drilling fluid. One of ordinary skill in the art with the benefit of this disclosure should recognize the appropriate amount of the aqueous liquid for a chosen application.

As previously described, one or more dissolved salts may also be present in the aqueous liquid. Where used, the dissolved salt may be included in the aqueous liquid for any purpose, including, but not limited to, densifying a drilling fluid including water to a chosen density. A mixture of one or more dissolved salts and water may be used in some instances. The amount of salt that should be added may be the amount needed to provide a desired density. One or more salts may be added to the water to provide a brine that includes the dissolved salt and the water. Suitable dissolved salts may include monovalent (group I) and divalent salts (group II). Mixtures of monovalent, divalent, and trivalent salts may also be used. Suitable salts may include, but are not limited to, calcium chloride, sodium chloride, sodium bromide, potassium bromide, potassium chloride, potassium formate, cesium formate, lithium chloride, lithium bromide sodium formate, lithium formate, ammonium chloride, organic cation salts such as tetramethyl ammonium chloride, choline chloride, and mixtures thereof among others. The salt may be provided in any amount or concentration such as unsaturated, saturated, supersaturated, and saturated with additional solids. For example, the salt may be provided in an amount in a range of about 1 wt. % to about 40 wt. % based on a total weight of the aqueous liquid. Alternatively, the salt may be present in the drilling fluid in an amount of about 1 wt. %, about 10 wt. %, about 20 wt. %, about 30 wt. %, or about 40 wt. % based on a total weight of the drilling fluid. One of ordinary skill in the art with the benefit of this disclosure should recognize the appropriate amount of the salt for a chosen application.

The drilling fluids may include an emulsifying surfactant. Emulsifying surfactants may include, without limitation, fatty amines, ethoxylated nonylphenols, fatty acids, fatty acid esters, and combinations thereof. In general, suitable emulsifying surfactants may have a Griffin's HLB (hydrophilic-lipophilic balance) of about 9 or greater may be suitable used. Fatty acids and fatty acid esters may be of particular interest as they are generally non-hazardous to the working environment and may pose little environmental risk. The Griffin's HLB values may be calculated by the following formula:

$$HLB = 20 * \frac{M_h}{M}$$

where $M_h$ is the molecular mass of the hydrophilic portion of the molecule and M is the molecular mass of the whole molecule. One of ordinary skill in the art with the benefit of this disclosure should be able to determine if a particular emulsifying surfactant includes a Griffin's HLB value of greater than about 9.

One of ordinary skill will appreciate that the emulsifying surfactants may be present in any amount suitable for a particular application. In some examples, without limitation, the emulsifying surfactant may be present in the drilling fluid in an amount ranging from about 0.5 wt. % to about 10 wt. % based on a total weight of the drilling fluid. Specific amounts of the emulsifying surfactant may include, but are not limited to about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, or about 10 wt. % based on a total weight of the drilling fluid. One of ordinary skill in the art with the benefit of this disclosure should recognize the appropriate amount of the emulsifying surfactant for a chosen application.

In addition, a weight agent may be included in the drilling fluid. Weighting agents are typically particulate materials with a high-specific gravity. As used herein, the term "high-specific gravity" refers to a material having a specific gravity greater than 2.6. Examples of suitable weighting agents may include, but are not limited to, barite, hematite, ilmentite, manganese tetraoxide, galena, calcium carbonate, and combinations thereof. The weight agent may be present in the drilling fluid in an amount sufficient for a particular application. For example, the weighting agent may be included in the drilling fluid to provide a particular density. Suitable amounts of the weighting agent may include, but are not limited to, the weighting agent present in the drilling fluid in an amount about to about 50% by volume of the drilling fluid (vol %) (e.g., about 5 vol %, about 15 vol %, about 20 vol %, about 25 vol %, about 30 vol %, about 35 vol %, about 40 vol %, about 4.5 vol % etc.). For example, the weighting agent may be present in the drilling fluid in an amount ranging from of about 10 vol % to about 40 vol %. One of ordinary skill in the art with the benefit of this disclosure should recognize the appropriate type and amount of the weighting agent for a chosen application.

A wide variety of additional additives may be included in the drilling fluids as desired for a particular application. Suitable additives may include, but are not limited to, clays, viscosifiers, shale stabilizers, wetting agents, and weighting agents, among others. Suitable viscosifiers may include, but are not limited to, water soluble starches and modified versions thereof, water-soluble polysaccharides and modified versions thereof, water soluble celluloses and modified versions thereof, water soluble polyacrylamides and copolymers thereof biopolymers, and combinations thereof. One of ordinary skill, with the benefit of this disclosure, should be able to select additional drilling fluid additives for a particular application.

Those of ordinary skill in the art will appreciate that the drilling fluid generally should have a density suitable for a particular application. By way of example, the drilling fluid may have a density in the range of from about 7 pounds per gallon ("lb/gal") (838.8 kg/m$^3$) to about 20 lb/gal (2397 kg/m$^3$). In certain embodiments, the drilling fluid may have a density in the range of from about 8 lb/gal (958.6 kg/m$^3$) to about 12 lb/gal (1438 kg/m$^3$). Those of ordinary skill in the art, with the benefit of this disclosure, should recognize the appropriate density for a particular application.

When drilling a wellbore, the drilling fluid may be continuously circulated from the well surface down to the bottom of the wellbore being drilled and back to the well surface again. As previously described, the density of the drilling fluid may be maintained, for example, control the hydrostatic pressure exerted by the drilling fluid against the subterranean formation. At times, circulation of the drilling fluid may be stopped for a period of time, e.g., for tripping of the drill string. When the drilling fluid remains static, particulates additives in the drilling fluid such as the weighting agents may settle, commonly referred to as sag. Because sag may have an undesirable on the properties of the drilling fluid, the drilling fluid may be monitored for sag.

The methods and systems disclosed may use EIS to monitor the sag behavior of drilling fluids. The systems and methods may be used to monitor the sag behavior of drilling fluid in a mud pit, on a rig, in a mud plant, in a laboratory, or at any other suitable location. Prior to using EIS to analysis the sag behavior of a drilling fluid tests may be performed to measure impedance of a drilling fluid as a function of frequency. An equivalent circuit model may then be used to fit the measured impedance data from which model parameters may be extracted. The model parameters may be correlated to drilling fluid properties to characterize sag behavior.

FIG. 1A illustrates an EIS fluid analysis system 100 that may be used to measure impedance for a drilling fluid. As illustrated, the EIS fluid analysis system 100 may include a container 102 and an EIS analyzer 104. Container 102 may be any suitable container for holding a sample fluid 114. A pair of plates 106 may be disposed in container 102. Plates 106 may have any suitable configuration. As illustrated, plates 106 may be generally parallel to one another. Plates 106 are considered generally parallel where they converge or diverge by no more than 5°. In addition, plates 106 are shown disposed in container 102 in a vertical configuration. While plates 106 are shown in the vertical configuration, it should be understood that plates 106 may be disposed in container 102 in other configurations, including, but not limited to, horizontal and angled configurations. It should understood that the plates 106 should be considered in a vertical configuration where the longitudinal axis of the plates 106 extend at angle of from 85° to 95° with respect to the horizontal plane. In one example, plates 106 may have a diameter ranging from about 1 inch (2.5 cm) to about 12 inches (30 cm) with a gap between plates 106 ranging from about 0.1 (0.25 cm) inches to about 1 inch (2.5 cm). For example, plates 106 may have a diameter of about 2 inches (5 cm) and a gap of about 0.19 inches (0.48 cm).

EIS analyzer 104 may be in signal communication with plates 106. As illustrated, lines 108, 110 may couple plates 106 to EIS analyzer 104. EIS analyzer 104 may measure impedances of sample fluid 114. The EIS analyzer 104 may include a signal generator 112. As illustrated, signal generator 112 is shown as a component of EIS analyzer 104, but signal generator 112 may also be separate from EIS analyzer 104. Signal generator 112 by way of EIS analyzer, for example, may apply an electric signal, such as an AC signal, to plates 106 so that the electric signal pass through sample fluid 114 in container 102. Lines 108, 110 may allow EIS analyzer 104 to capture measurements of sample fluid 114 during application of the electrical signal. By way of example, the EIS analyzer 104 may determine current through sample fluid 114 in container 102, the potential difference across the sample fluid 114 in container 102, and/or the phase angle θ. From these measurements, the real and imaginary parts of the impedance may be determined.

In operation, the EIS fluid analysis system 100 may be used to measure the impedance of sample fluid 114 over time. As shown in FIG. 1A, sample fluid 114, which may be a drilling fluid, may be placed in container 102. Particulate additives 116, such as a weighting agent, may be included in sample fluid 114. Over time, particulate additives 116 in sample fluid 114 may settle. As illustrated by FIG. 1B, the settling of particulate additives 116 may result in stratification of sample fluid 114 into a light fraction 118 and a heavy fraction 120. The light fraction 118 may be considered a solids-depleted section. The heavy fraction 120 may be considered a solids-loaded section. While not separately shown, solids may collect and build up in the bottom of container 102. By taking impedance measurements over time while particulate additives 116 are settling in sample fluid 114, the present systems and methods may be used to determine sag behavior of sample fluid 114.

FIG. 2 illustrates an alternative configuration of EIS fluid analysis system 100. As illustrated, EIS fluid analysis system 100 may include a container 102 and an EIS analyzer 104. Plates 106 may be disposed in container 102. In contrast to the plates 106 shown on FIG. 1 in a vertical configuration, plates 106 illustrated on FIG. 2 are in a horizontal configuration. It should understood that the plates 106 should be considered in a horizontal configuration where the longitudinal axis of the plates 106 extend at angle of from −5° to 5° with respect to the horizontal plane.

Figure 3:
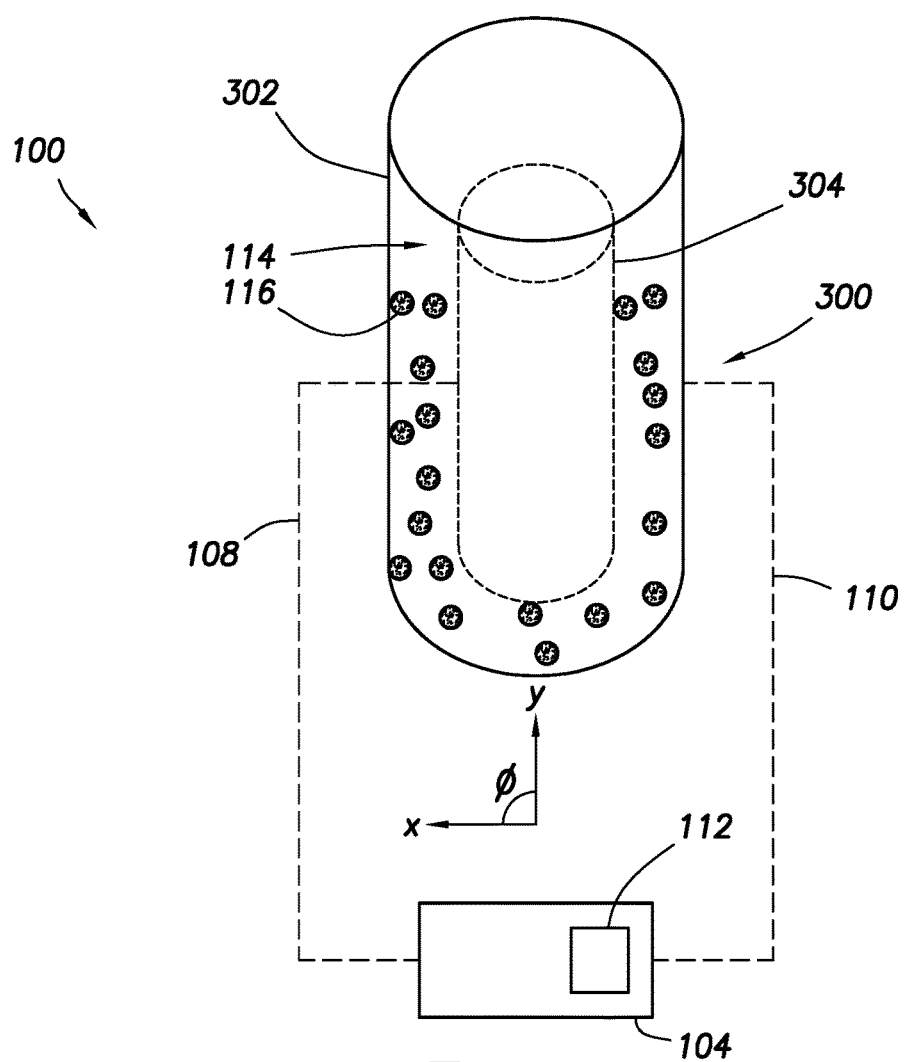
FIG. 3 illustrates an embodiment of an EIS fluid analysis system having a concentric cylinder probe.

FIG. 3 illustrates another alternative configuration of EIS fluid analysis system 100. As illustrated, EIS fluid analysis system 100 may be in the form of a concentric cylinder probe 300 that includes an outer cylindrical container 302 and an inner cylinder 304. Outer cylindrical container 302 may be any suitable container for holding a sample fluid 114 that includes particulate additives 116. Inner cylinder 304 may be disposed in outer cylindrical container 302. Sample fluid 114 may be disposed in the gap between outer cylindrical container 302 and inner cylinder 304. In this example, an excitation signal may be sent from outer cylindrical container 302 to inner cylinder 304 through sample fluid 114. The excitation signal may also be sent in the opposite direction from inner cylinder 304 to outer cylindrical container 302. The inner cylinder 304 may be hollow, solid, or otherwise configured. In addition while the concentric cylinder probe 300 is shown in a cylindrical configuration, other configurations of a concentric sample probe that use an outer container and an inner container to send an excitation signal through sample fluid 114 may be used. Concentric cylinder probe 300 is shown in a vertical configuration. While concentric cylinder probe 300 is shown in the vertical configuration, it should be understood that concentric cylinder probe 300 may disposed in other configurations, including, but not limited to, horizontal and angled configurations. It should be understood that concentric cylinder probe 300 should be considered in a vertical configuration where angle θ of concentric cylinder probe 300 from horizontal is from 85° to 95°. In angled configurations, concentric cylinder probe 300 may be disposed at an angle, for example, of about 10° to 85°, and alternatively, from about 30° to 75°. EIS analyzer 104 may be in signal communication with concentric cylinder probe 300. As illustrated, lines 108, 110 may couple inner cylinder 304 to EIS analyzer 104.

EIS analyzer 104 may measure impedances of sample fluid 114. The EIS analyzer 104 may include a signal generator 112. As illustrated, signal generator 112 is shown as a component of EIS analyzer 104, but signal generator 112 may also be separate from EIS analyzer 104. Signal generator 112 by way of EIS analyzer, for example, may apply an electric signal, such as an AC signal, to inner cylinder 304 so that the electric signal pass through sample fluid 114 in outer cylindrical container 302. Lines 108, 110 may allow EIS analyzer 104 to capture measurements of sample fluid 114 during application of the electrical signal.

EIS measurements of sample fluid 114 may be taken over time. Typically, impedance $Z(\omega)$ of a fluid at an angular frequency $\omega=2\pi f$ is given by $Z(\omega)=Z'(\omega)+iZ''(\omega)$, where $Z'(\omega)$ is the real part (i.e., resistance) of the impedance and $Z''(\omega)$ is the imaginary part (i.e., reactance) of the impedance. The variation in the impedance in the angular frequency can be represented using a Nyquist plot.

FIGS. 4-7 Nyquist plot illustrates the frequency response for a sample fluid 114 (e.g., a drilling fluid) at different times. Specifically, FIGS. 4-7 depict the variation in the impedance of sample fluid 114 due to variation in angular frequency. In FIGS. 4-7, the resistance (or real part of the impedance) is represented on x-axis while the reactance (or imaginary part of the impedance) is represented on the y-axis. For the measurements shown on FIGS. 4-7, the AC signal frequency was varied from 20 Hz to 100 kHz. The measurements were taken at room temperature. The sample fluid 114 had a density of 10 pounds per gallon (1.2 kilograms per liter) and an oil-to-water weight ratio of 95/5 for FIGS. 4 and 5 and 80/20 for FIGS. 6 and 7. The weighting agent used was barite in an amount of 160 pounds per barrel (456 kg per cubic meter).

Figure 4:
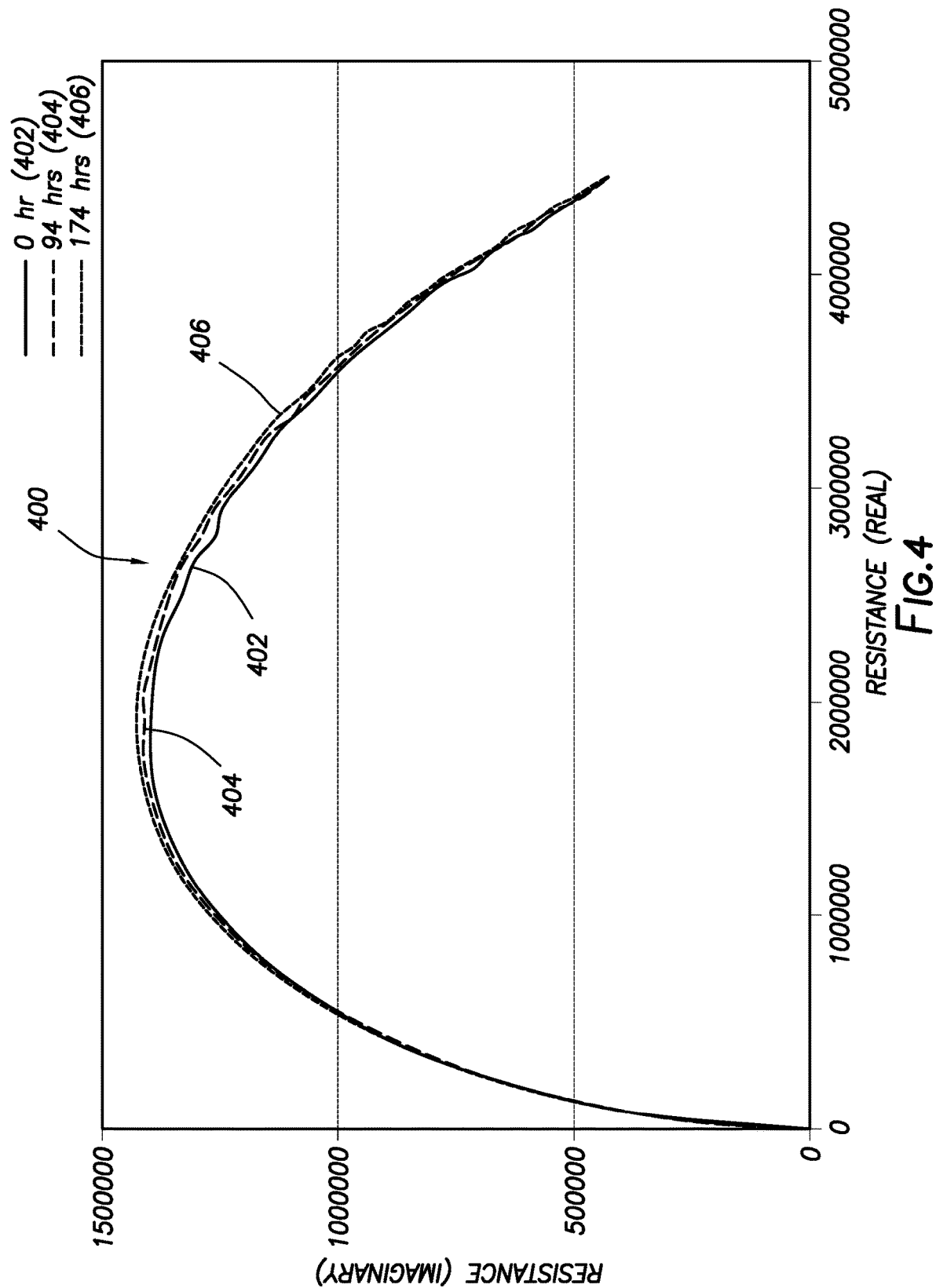
FIG. 4 illustrates Nyquist plots of a drilling fluid at different times using an EIS fluid analysis system having a pair of parallel plates in a vertical configuration.

In FIG. 4, a Nyquist plot 400 is shown for impedance measurements taken over time using an EIS fluid analysis system 100 as shown in FIG. 1A with plates 106 in a vertical configuration. Nyquist plot 400 depicts a curve 402, curve 404, and curve 406 for measurements taken at 0 hours, 94 hours, and 174 hours, respectively. Specifically, the Nyquist plot 400 illustrates the variation in impedance over time. As illustrated, the change of impedance over time is minor due to slow sedimentation of the particulate additives 116.

Figure 5:
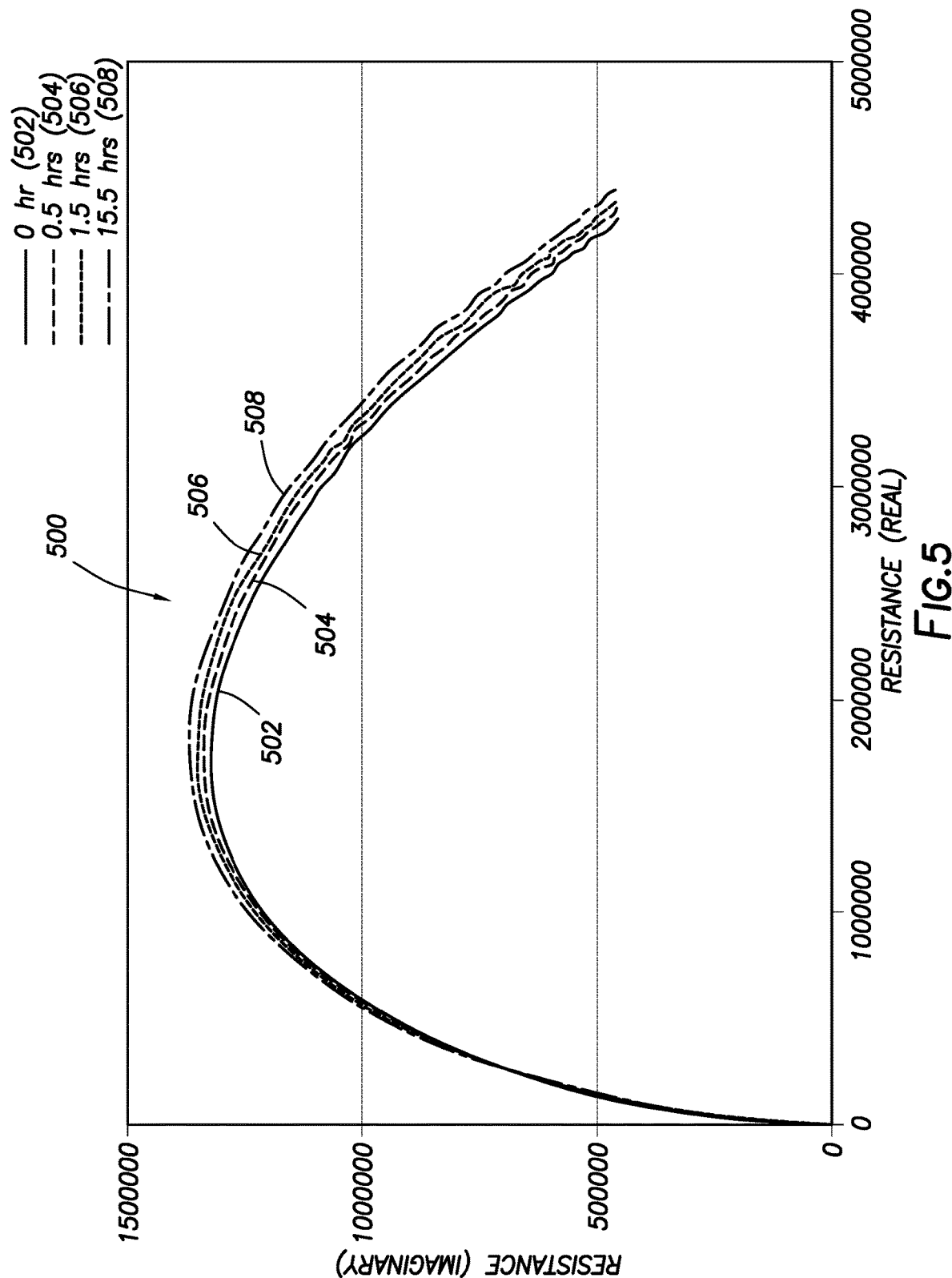
FIG. 5 illustrates Nyquist plots of a drilling fluid at different times using an EIS fluid analysis system having a pair of parallel plates in a horizontal configuration.

FIG. 5 illustrates a Nyquist plot 500 for impedance measurements taken over time using an EIS fluid analysis system 100 as shown in FIG. 2 with plates 106 in a horizontal configuration. Nyquist plot 500 depicts a curve 502, curve 504, curve 506, and curve 508 for measurements taken at 0 hours, 0.5 hours, 1.5 hours, and 15.5 hours, respectively. Specifically, the Nyquist plot 500 illustrates the variation in impedance over time. As illustrated, the change of impedance over time is more pronounced in FIG. 5 for the horizontal configuration than shown in FIG. 4 for the vertical configuration. It is believe that this difference may be due to the travel distance of particulate additives 116 during sedimentation. For the vertical configuration, particulate additives 116 may travel up to 2 inches (5 cm), for example, to show the impact of the impedance measurement. However, for the horizontal configuration, the particulates additives 116 only need to travel the distance of the gap, for example, up to 0.19 inches (0.48 cm), to show the impact of the impedance measurement. Regardless of the speed of sedimentation, both vertical and horizontal configurations may be used to analyze sag of sample fluid 114.

Figure 6:
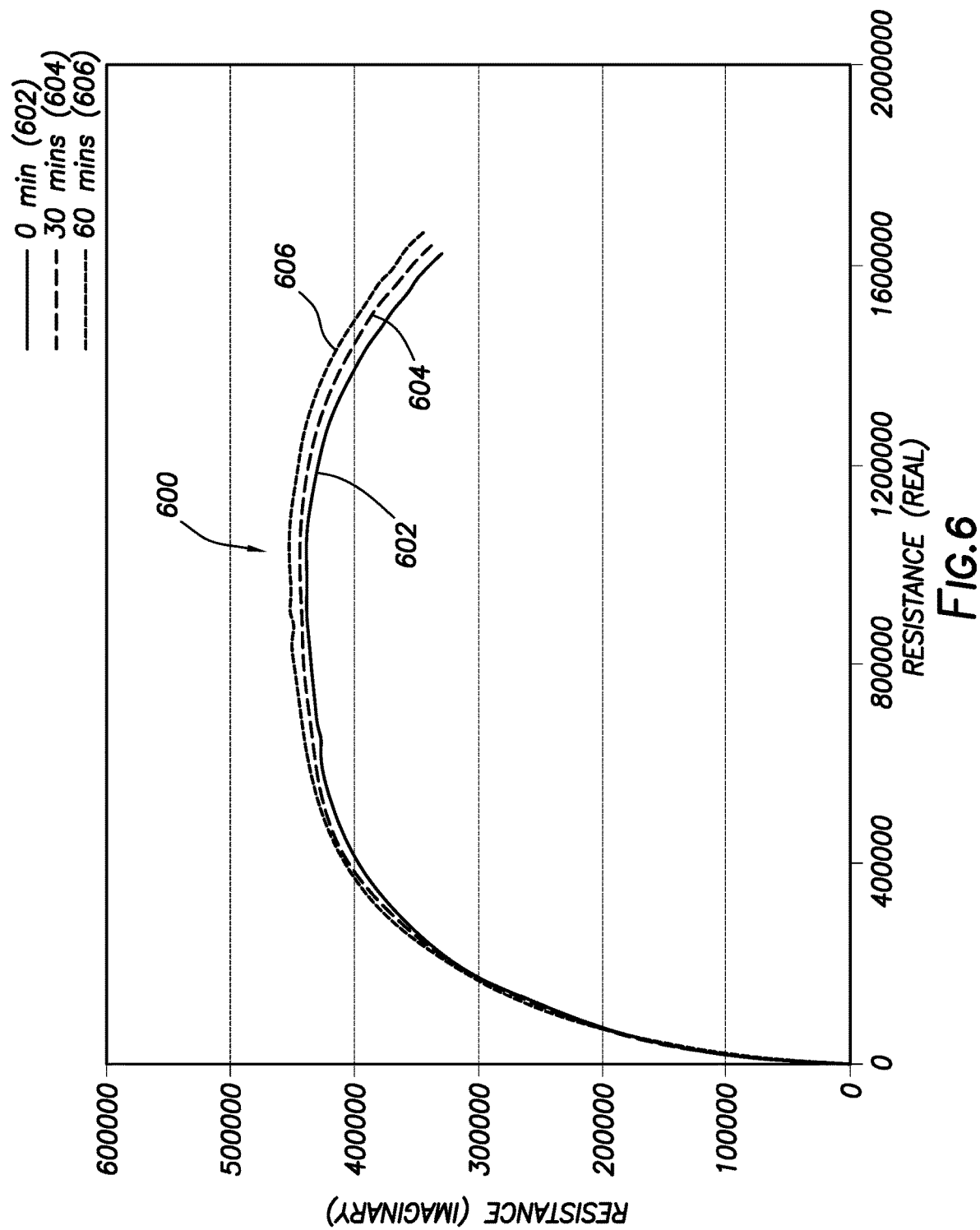
FIG. 6 illustrates Nyquist plots of a drilling fluid at different times using an EIS fluid analysis system having a concentric cylinder probe in a vertical configuration.

FIG. 6 illustrates a Nyquist plot 600 for impedance measurements taken over time using an EIS fluid analysis system 100 as shown in FIG. 3 with concentric cylinder probe 300 in a vertical configuration. Outer cylindrical container 302 had a diameter of 0.68 inches (1.7 cm) and inner cylinder 304 had a diameter of 0.58 in (1.5 cm). The length of the outer cylindrical container 302 and inner cylinder 304 was 2.5 inches (6.4 cm). Nyquist plot 600 depicts a curve 602, curve 604, and curve 606 for measurements taken at 0 minutes, 30 minutes, and 60 minutes. Specifically, the Nyquist plot 600 illustrates the variation in impedance over time.

Figure 7:
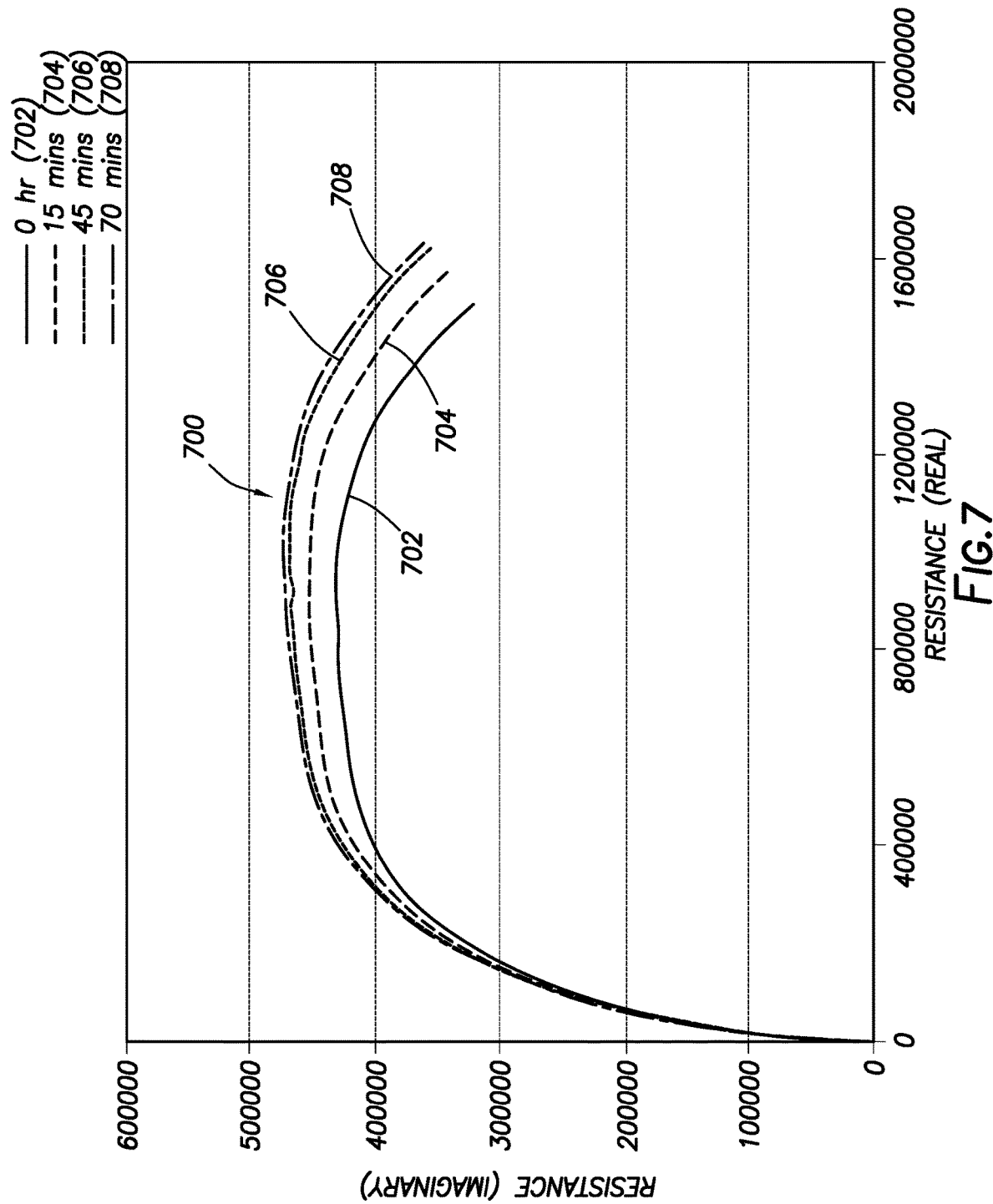
FIG. 7 illustrates Nyquist plots of a drilling fluid at different times using an EIS fluid analysis system having a concentric cylinder probe in an angled configuration.

FIG. 7 illustrates a Nyquist plot 700 for impedance measurements taken over time using an EIS fluid analysis system 100 as shown in FIG. 3 with concentric cylinder probe 300 in angled configuration. In particular, concentric cylinder probe 300 was disposed at an angle ϕ of 57°. Outer cylindrical container 302 had a diameter of 0.68 inches (1.7 cm) and inner cylinder 304 had a diameter of 0.58 in (1.5 cm). The length of the outer cylindrical container 302 and inner cylinder 304 was 2.5 inches (6.4 cm). In FIG. 7, Nyquist plot 700 depicts a curve 702, curve 704, curve 706, and curve 708 for measurements taken at 0 minutes, 15 minutes, 45 minutes, and 70 minutes. Specifically, the Nyquist plot 700 illustrates the variation in impedance over time. As compared to Nyquist plot 600 in FIG. 6, Nyquist plot 700 of the impedance profile on FIG. 7 shows significant difference depending on the orientation of concentric cylinder probe 300, due to the different particle sedimentation accelerations.

Figure 8:
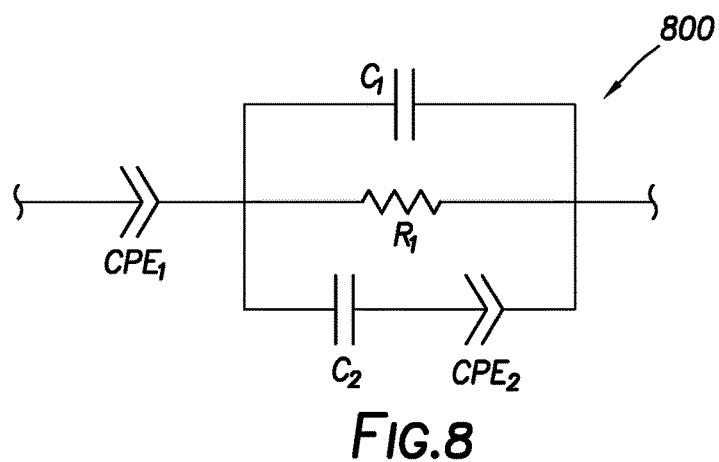
FIG. 8 illustrates an equivalent circuit model for simulating data from an EIS fluid analysis system.

The impedance of the sample fluid 114 (e.g. a drilling fluid) depicted in FIGS. 4-7 may be simulated using an equivalent circuit model. FIG. 8 illustrates an equivalent circuit model 800 for simulating the frequency responses of the sample fluid 114 depicted in Nyquist plots 400-700 of FIGS. 4-7, respectively, for different times. Any suitable equivalent circuit model that can singularly simulate (model) the frequency responses for sample fluid 114 may be used.

As illustrated, the equivalent circuit model 800 may include various model elements, including a first capacitor C1, a second capacitor C2, a resistor R1, and first and second constant phase elements CPE1 and CPE2, respectively. The equivalent circuit impedance ($Z_{eq}$) may be given by:

$$Z_{eq}(\omega) = Z_{CPE1}(\omega) +$$

$$\frac{Z_{R1}Z_{C1}(\omega)(Z_{C2}(\omega) + Z_{CPE2}(\omega))}{Z_{C1}(\omega)(Z_{C2}(\omega) + Z_{CPE2}(\omega)) + Z_{R1}(Z_{C1}(\omega) + Z_{C2}(\omega) + Z_{CPE2}(\omega))}$$

Where $Z_{C1}$, $Z_{C2}$, $Z_{R1}$, $Z_{CPE1}$, $Z_{CPE2}$ represent the impedances of the capacitors C1 and C2, resistor R1, and constant phase elements CPE1 and CPE2, respectively. The complex impedances for each model element may be given by:

$$Z_{R1}(\omega) = R_1$$

$$Z_{C1}(\omega) = \frac{1}{i\omega C1}$$

$$Z_{C2}(\omega) = \frac{1}{i\omega C2}$$

$$Z_{CPE1}(\omega) = \frac{1}{p_1(i\omega)^{n_1}}$$

$$Z_{CPE2}(\omega) = \frac{1}{p_2(i\omega)^{n_2}}$$

The capacitive or resistive nature of the constant phase elements CPE1 and CPE2 may be determined based on the values of n1 and n2. When n1=1, CPE1 represents an ideal capacitor and p1 represents the value of the capacitance of the capacitor CPE1. When n1=0, CPE1 represents an ideal resistor and p1 represents the value of the resistance of the resistor CPE1. For a value of n1 between 0 and 1 (0<n1, 1), CPE1 represents a non-ideal capacitor. Similarly, when n2=1, CPE2 represents an ideal capacitor and p2 represents the value of the capacitance of the capacitor CPE2 and when n2=0, CPE2 represents an ideal resistor and p2 represents the value of the resistance of the resistor CPE2. For a value of n2 between 0 and 1 (0<n2, 1), CPE2 represents a non-ideal capacitor.

Figure 9:
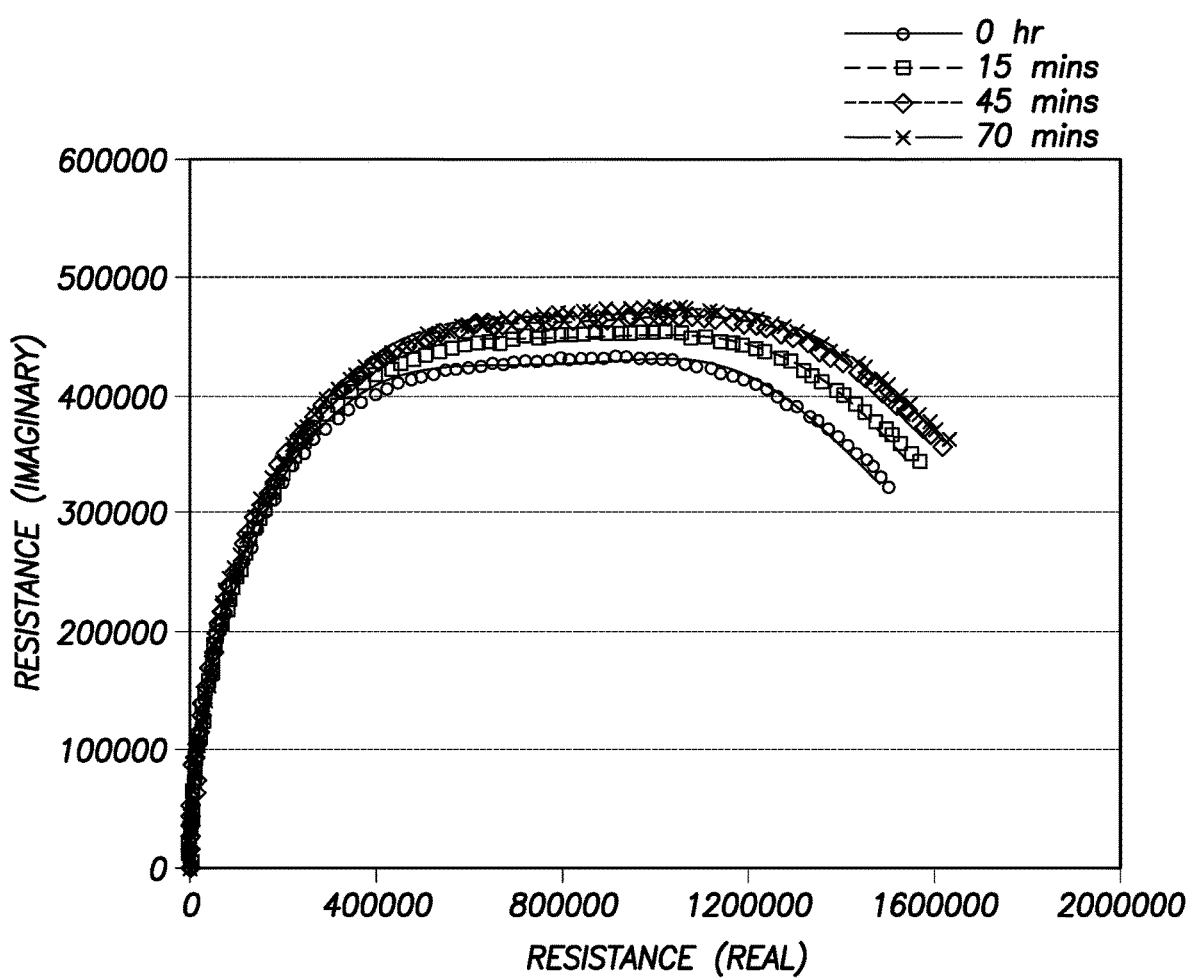
FIG. 9 illustrates Nyquist plots of a drilling fluid at different times showing an example of a fitted model prediction to experimental data.

In an example, the values of each model element C1, C2, R1, CPE1, and CPE2 of the equivalent circuit model 800 may be determined using a complex least-square fitting procedure that minimizes a desired objective function. The desired objective function may be given by:

$$\min \text{Sum} = \sum_{k=1}^{N} w_k \cdot \{[Z'(\omega_k) - Z'_{eq}(\omega_k)]^2 + [Z''(\omega_k) - Z''_{eq}(\omega_k)]^2\}$$

Where k represents the $k^{th}$ measured data point at angular frequency $\omega_k$, Z' is the real part of the measured impedance, Z" is the imaginary part of the measured impedance, and $w_k$ is the optional weight used at each data point. FIG. 9 shows an example of the fitted model prediction to the experimental data shown in FIG. 7. The change of impedance at the frequency may be correlated with sag. By way of example, the integral of the curves or values at a frequency may be correlated to a settling velocity. The frequency may be fixed at any suitable amount, including 5000 Hz or less.

After the parameters may be extracted from the measured data, correlations between the model parameters and the sag of the drilling fluid may be established. These parameters may be used to characterize the sedimentation of a drilling fluid. Parameters R1 and p1 were both was extracted from measured data obtained using concentric cylinder probe 300 of FIG. 3 in both the vertical configuration and angled configuration (e.g., 57°).

Figure 10:
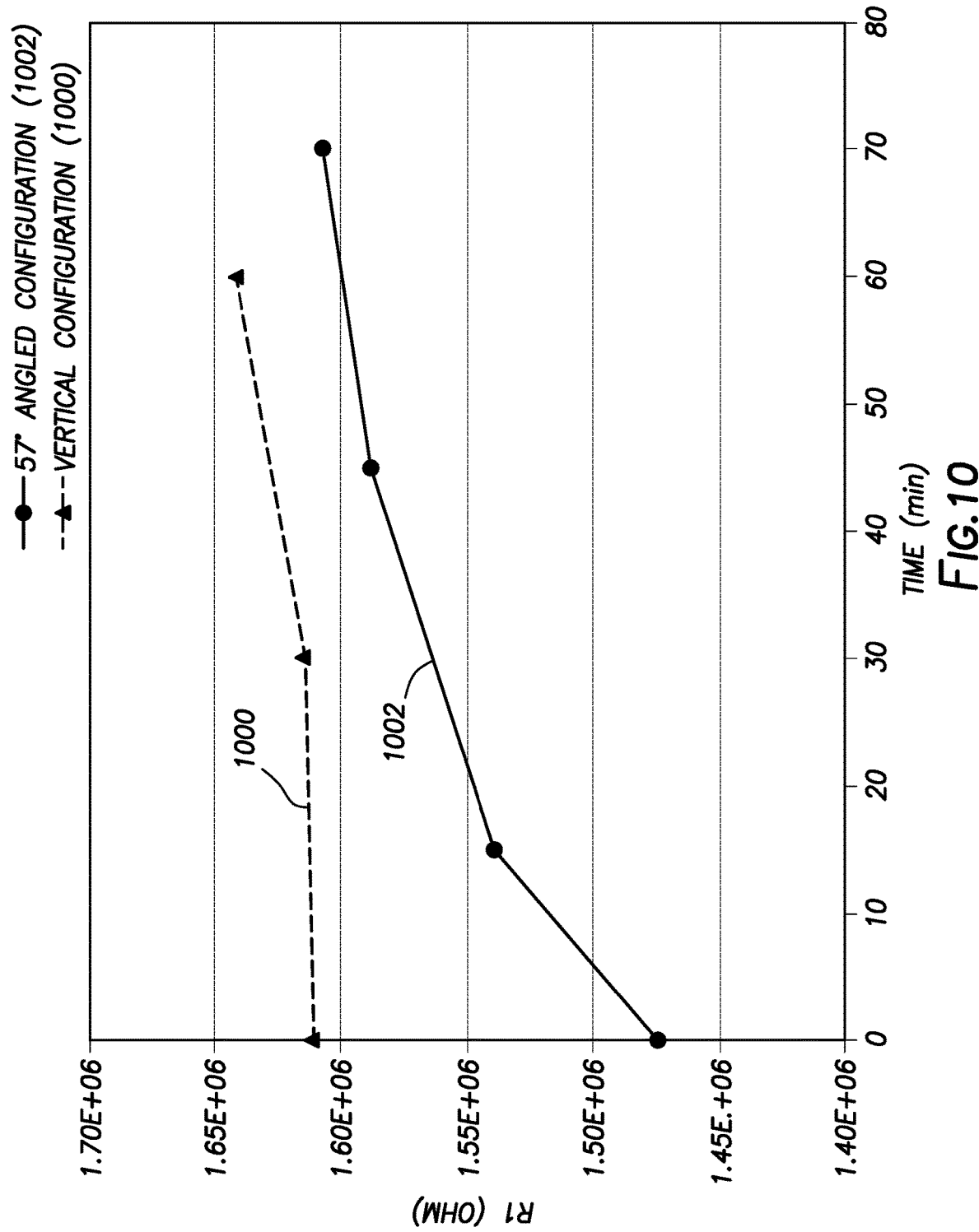
FIG. 10 illustrates an example calibration curve correlating a model parameter as a function of time.
Figure 11:
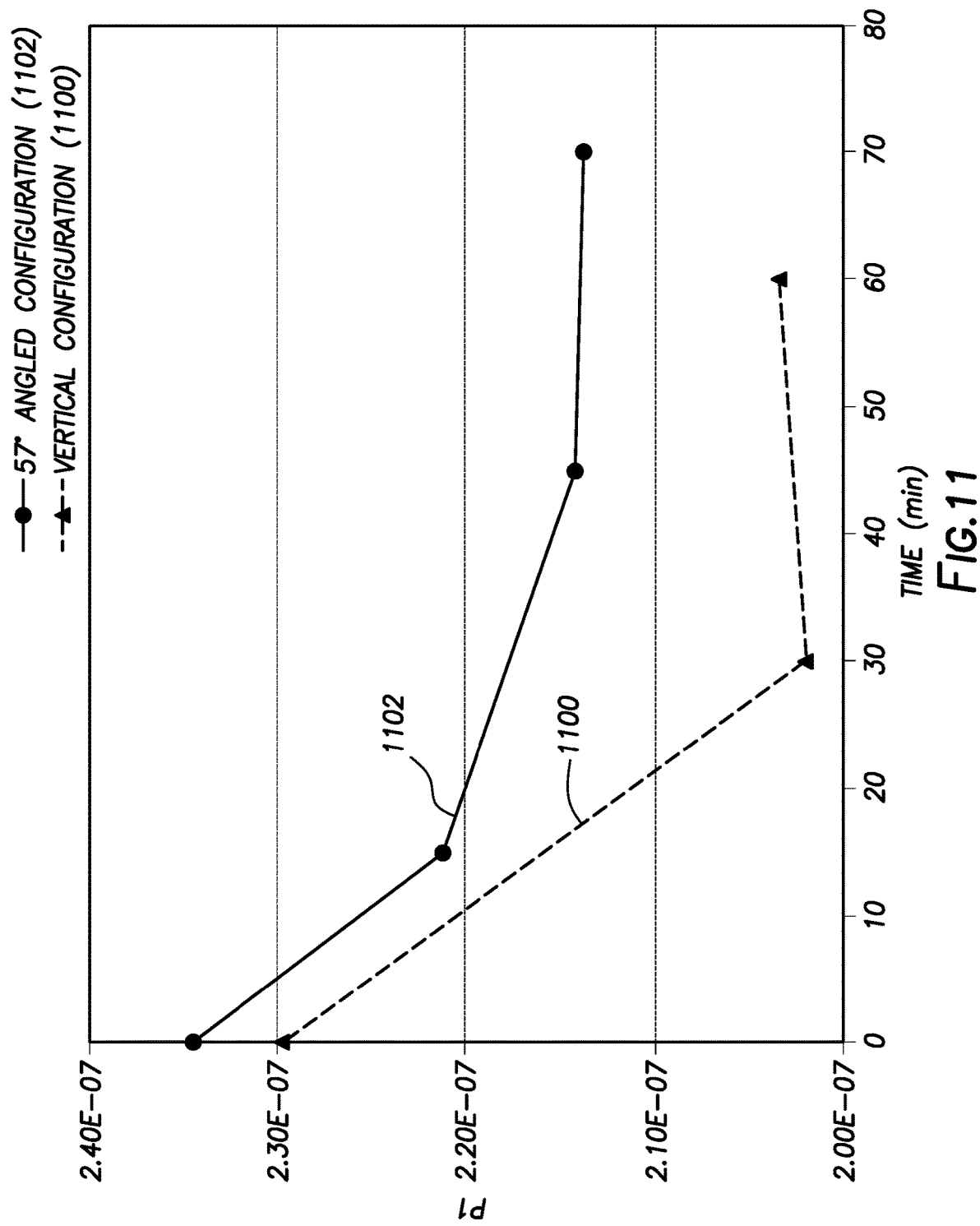
FIG. 11 illustrates an example calibration curve correlating another model parameter as a function of time.

FIG. 10 illustrates model parameter R1 that was extracted as a function of time. On FIG. 10, are curve 1000 and curve 1002 for the measurements from the vertical configuration and angled configuration, respectively. As illustrated, the parameter R1 may increase over time for both vertical and angled configurations of concentric cylinder probe 300. P FIG. 11 illustrates model parameter p1 that was extracted as a function of time. On FIG. 11, are curve 1100 and curve 1102 for the measurements from the vertical configuration and angled configuration, respectively. As illustrated, the parameter p1 may increase over time for both vertical and angled configurations of concentric cylinder probe 300. While FIGS. 10 and 11 use model parameters R1 and p1 to illustrate the sag of a drilling fluid, other model parameters could also be used.

Figure 12:
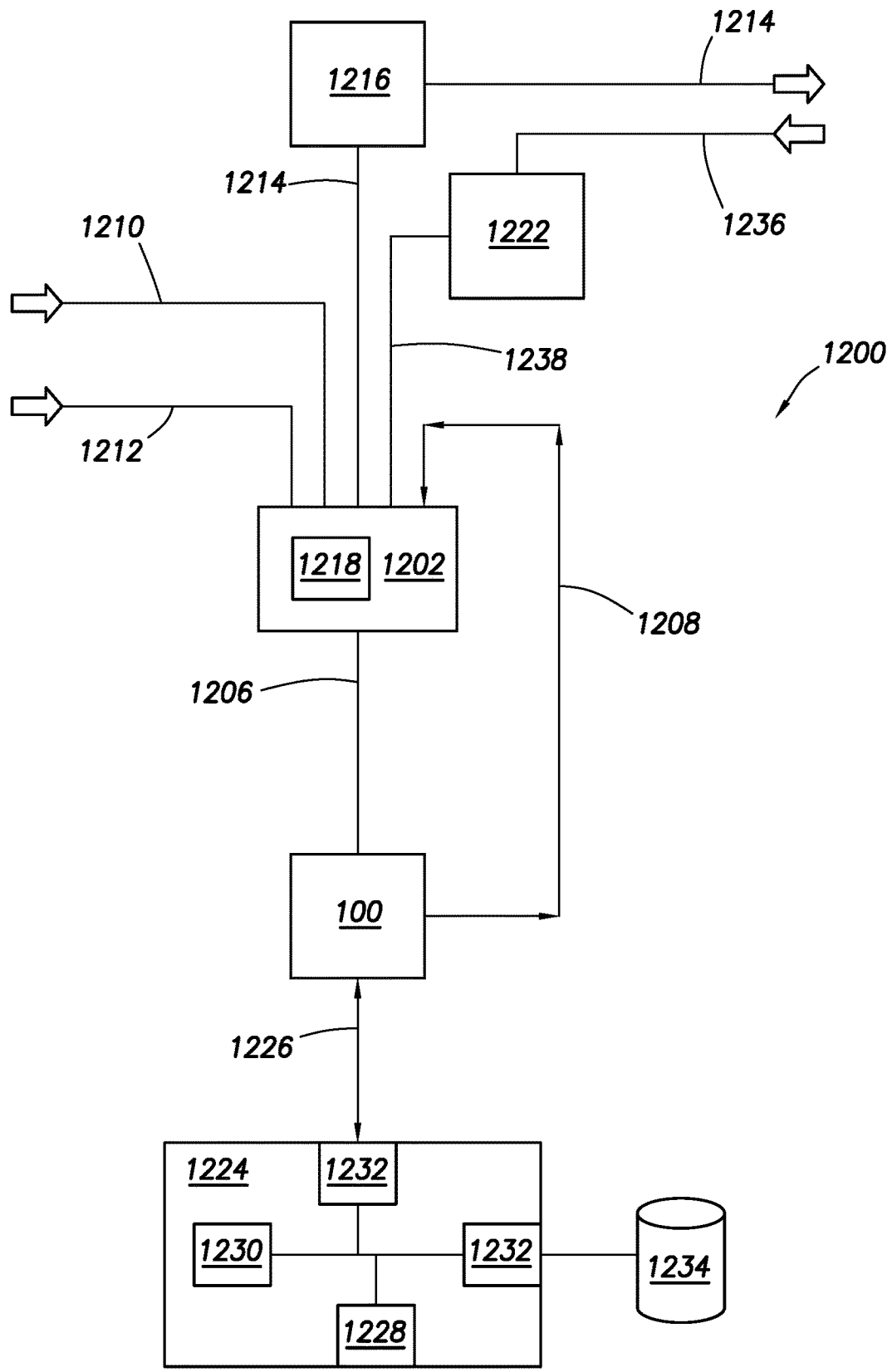
FIG. 12 illustrates a block diagram of a drilling fluid monitoring and handling system.

FIG. 12 illustrates a block diagram of a drilling fluid monitoring and handling system 1200 for determining concentration of one or more components of drilling fluids. As illustrated, the fluid monitoring and handling system 1200 may generally include a mud pit 1202 and a EIS fluid analysis system 100. A portion of the drilling fluid from the mud pit 1202 may be fed via a mud pit line 1206 to the EIS fluid analysis system 100, which may be configured to perform electro-rheology measurements on the portion of the drilling fluid supplied thereto. The EIS fluid analysis system 100 may analyze the drilling fluid using the example method disclosed above with respect to FIGS. 1-11. After fluid analysis, the portion of the drilling fluid may be returned to mud pit 1202 via a return line 1208.

The mud pit 1202 may be any vessel suitable for holding a drilling fluid. For example, the mud pit 1202 may include a container such as a drum or tank, or a series of containers that may or may not be connected. The mud pit 1202 may be supplied with the drilling fluid from an initial drilling fluid supply line 1210 that provides an initial supply of drilling fluid to the mud pit 1202. However, the initial supply of drilling fluid does not imply that the drilling fluid has not been recycled or circulated in a wellbore, but simply indicates that this supply is not presently being circulated or otherwise used in the wellbore.

Drilling fluid additives (e.g., weighting agents, emulsifying agents, clay, viscosifiers, etc.) may be added via a drilling fluid additive supply line 1212 to the mud pit 1202, if desired, and based on the analysis provided by the EIS fluid analysis system 100. Alternatively or additionally, in an example, the results of the analysis may be used to modify the manufacturing process of the drilling fluid. After the drilling fluid additives have been added to the drilling fluid, the drilling fluid may be retested using the EIS fluid analysis system 100 to verify the drilling fluid was correctly formulated or the drilling fluid may be sent to the wellbore for use in drilling operations via a wellbore line 1214 by way of mud pump 1216.

The mud pit 1202 may include a mixing system 1218 to mix the contents of the mud pit 1202 as well as any drilling fluid additives. For instance, the mixing system 1218 may mix the drilling fluid in the mud pit 1202 with drilling fluid from the initial drilling fluid supply line 1210, drilling fluid from the return line 1208, drilling fluid additives, additional non-aqueous fluids, aqueous fluids or combinations thereof. In general, the mixing system 1218 may be configured to prevent solids within the drilling fluid from settling. The mixing system 1218 may use any suitable mixing technique for mixing of the drilling fluid. For instance, the mixing system 1218 may include a static mixer, dynamic mixer, or other suitable mixer. The mud pit 1202 may further include suitable pumping equipment (not shown) t to pump the drilling fluid in the mud pit 1202 to the EIS fluid analysis system 100 via mud pit line 1206.

The EIS fluid analysis system 100 may analyze the portion of the drilling fluid in a continuous or non-continuous manner, as desired, and based on whether flow through EIS fluid analysis system 100 is continuous or non-continuous. Although the EIS fluid analysis system 100 is shown at the mud pit 1202, examples disclosed herein contemplate the placement of EIS fluid analysis system 100 at any point in the fluid monitoring and handling system 1200. For example, EIS fluid analysis system 100 (or a portion thereof) may alternatively be placed in a fluid reconditioning system 1222 (discussed below), the mud pit 1202, as well as within the wellbore or in an exit conduit from the wellbore. As such, examples disclosed herein contemplate measuring the impedance at any point in the drilling fluid handling process, so that the drilling fluid may be monitored and/or subsequently adjusted as desired.

The analysis performed by EIS fluid analysis system 100 may be performed in collaboration with a computer system 1224 communicably coupled thereto. As illustrated, the computer system 1224 may be an external component of the EIS fluid analysis system 100, however, the computer system 1224 may alternatively include an internal component of the EIS fluid analysis system 100, without departing from the scope of the disclosure. The computer system 1224 may be connected to the EIS fluid analysis system 100 via a communication link 1226. The communication link 1226 may include a direct (wired) connection, a private network, a virtual private network, a local area network, a WAN (e.g., an Internet-based communication system), a wireless communication system (e.g., a satellite communication system, telephones), any combination thereof, or any other suitable communication link.

The computer system 1224 may be any suitable data processing system including, but not limited to, a computer, a handheld device, or any other suitable device. The computer system 1224 may include a processor 1228 and a non-transitory computer readable storage medium 1230 communicatively coupled to the processor 1228. The processor 1228 may include one central processing unit or may be distributed across one or more processors in one or more locations. Examples of a non-transitory computer readable storage medium 1230 include random-access memory (RAM) devices, read-only memory (ROM) devices, optical devices (e.g., CDs or DVDs), disk drives, and the like. The non-transitory computer readable storage medium 1230 may store computer readable program code that may be executed by the processor 1228 to process and analyze the measurement data generated by EIS fluid analysis system 100, adjust the parameters of the fluid monitoring and handling system 1200, and/or operate a part or whole of the fluid monitoring and handling system 1200. Further, from the impedance measurements of the drilling fluid measured by the EIS fluid analysis system 100, the program code may be executed by the processor 1228 to determine concentration of one or more drilling fluid additives (e.g., weighting agents) in the drilling fluid. The concentration may be determined, for example, using a correlation developed using electro-rheology. For example, the concentration may be determined using a correlation between a rate of change of at least one model parameter of an equivalent circuit model (e.g., equivalent circuit model 800 on FIG. 8).

The computer system 1224 may further include one or more input/output ("I/O") interface(s) 1232 communicatively coupled to the processor 1228. The I/O interface(s) 1232 may be any suitable system for connecting the computer system 1224 to a communication link, such as a direct connection, a private network, a virtual private network, a local area network, a wide area network ("WAN"), a wireless communication system, or combinations thereof; a storage device, such as storage 1234; an external device, such as a keyboard, a monitor, a printer, a voice recognition device, or a mouse; or any other suitable system. The storage 1234 may store data required by the EIS fluid analysis system 100 for performing fluid analysis. For instance, the storage 1234 may store a collection of equivalent circuit models that may be used during the EIS analysis. The storage 1234 may be or include compact disc drives, floppy drives, hard disks, flash memory, solid-state drives, and the like. Those of ordinary skill in the art will appreciate that suitable data processing systems may include additional, fewer, and/or different components than those described for computer system 1224.

Data processing and analysis software native to the EIS fluid analysis system 100 and/or installed on the computer system 1224 may be used to analyze the data generated by EIS fluid analysis system 100. This procedure may be automated such that the analysis happens without the need for operator input or control. Further, the operator may select from several previously input parameters or may be able to recall previously measured data. Any of the data may be transferred and/or stored on an external memory device (e.g., a USB drive), if desired.

With continued reference to FIG. 12, the drilling fluid may delivered to a wellbore from mud pit 1202 by way of mud pump 1216 via wellbore line 1214. The mud pump 1216 may be any type of pump or pumping system useful for circulating a drilling fluid into a subterranean formation under a sufficient pressure. The drilling fluid that has been circulated within the wellbore may be returned to the mud pit 1202 via a circulated drilling fluid return line 1236 and provided to a fluid reconditioning system 1222 to condition the circulated drilling fluid prior to returning it to the mud pit 1202. The fluid reconditioning system 1222 may be or include one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The fluid reconditioning system 1222 may further include one or more sensors, gauges, pumps, compressors, and the like used to monitor, regulate, and/or recondition the drilling fluid and various additives added thereto. After the drilling fluid has been reconditioned, the drilling fluid may be returned to the mud pit 1202 via the reconditioned fluid line.

Figure 13:
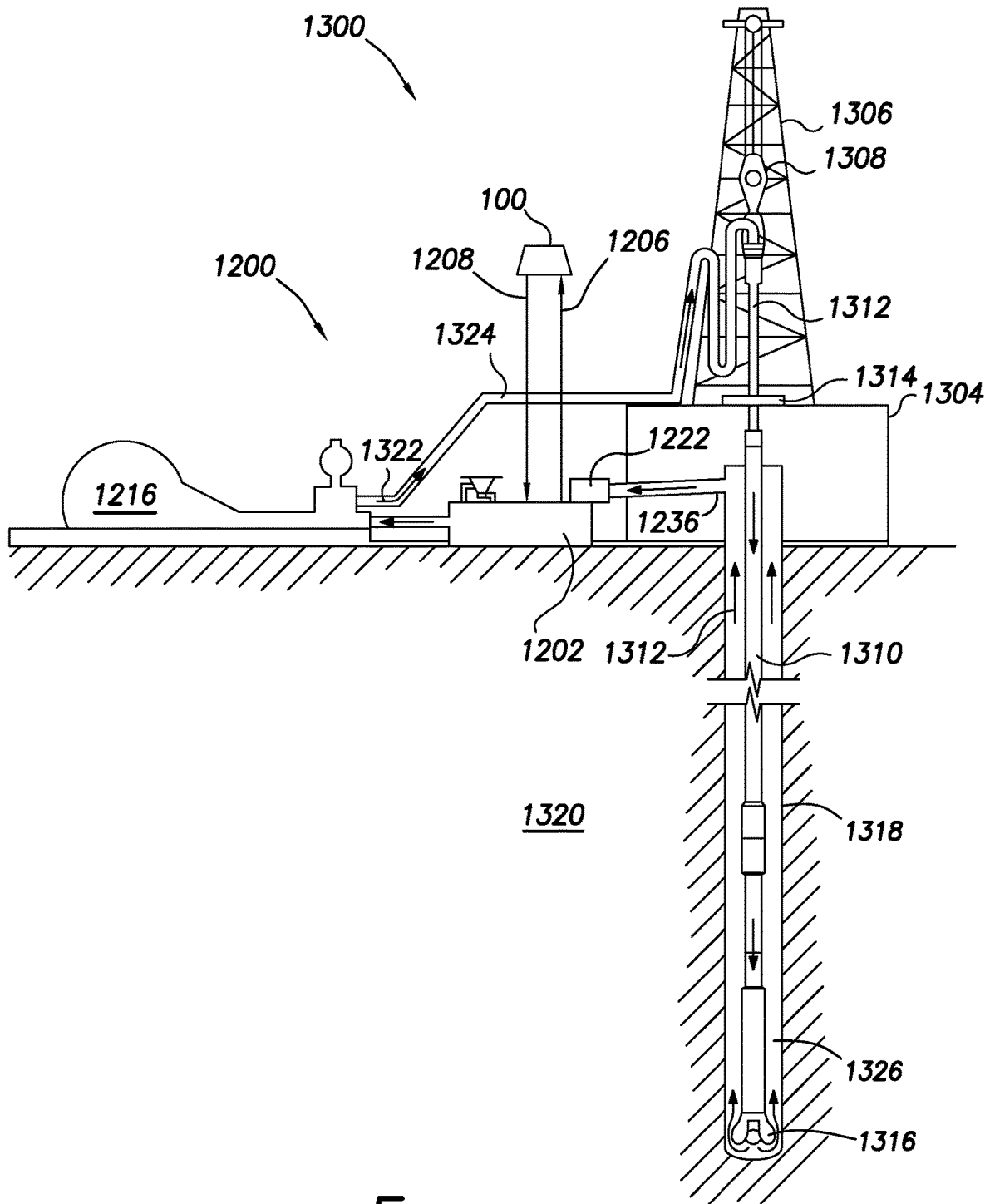
FIG. 13 illustrates an example drilling assembly that incorporates the drilling fluid monitoring and handling system of FIG. 14.

FIG. 13 illustrates an example of a drilling system 1300 that may employ the fluid monitoring and handling system 1200 of FIG. 12 described herein to determine concentration of one or more drilling fluid additives. It should be noted that while FIG. 13 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling system 1300 may include a drilling platform 1304 that supports a derrick 1306 having a traveling block 1308 for raising and lowering a drill string 1310. The drill string 1310 may include, but is not limited to, drill pipe and coiled tubing, as generally known to those skilled in the art. A kelly 1312 may support the drill string 1310 as it may be lowered through a rotary table 1314. A drill bit 1316 may be attached to the distal end of the drill string 1310 and may be driven either by a downhole motor and/or via rotation of the drill string 1310 from the well surface. Without limitation, the drill bit 1316 may include, roller cone bits, PDC bits, natural diamond bits, any hole openers, reamers, coring bits, and the like. As the drill bit 1316 rotates, it may create a wellbore 1318 that penetrates various subterranean formations 1320.

The drilling system 1300 may further include the fluid monitoring and handling system 1200 as generally described herein. The mud pump 1216 of the fluid monitoring and handling system 1200 representatively includes any conduits, pipelines, trucks, tubulars, and/or pipes used to fluidically convey the drilling fluid 1322 downhole, any pumps, compressors, or motors (e.g., topside or downhole) used to drive the drilling fluid 1322 into motion, any valves or related joints used to regulate the pressure or flow rate of the drilling fluid 1322, and any sensors (e.g., pressure, temperature, flow rate, etc.), gauges, and/or combinations thereof, and the like.

The mud pump 1216 may circulate may circulate the drilling fluid 1322 through a feed pipe 1324 and to the kelly 1312, which conveys the drilling fluid 1322 downhole through the interior of the drill string 1310 and through one or more orifices in the drill bit 1316. The drilling fluid 1322 may then be circulated back to the surface via an annulus 1326 defined between the drill string 1310 and the walls of the wellbore 1318. At the surface, the recirculated or spent drilling fluid 1322 may be conveyed to the fluid reconditioning system 1222 via a circulated drilling fluid return line 1236. After passing through the fluid reconditioning system 1222, a "cleaned" drilling fluid 1322 may be deposited into a nearby mud pit 1202. While illustrated as being arranged at the outlet of the wellbore 1318 via the annulus 1326, those skilled in the art will readily appreciate that the fluid reconditioning system 1222 may be arranged at any other location in the drilling system 900 to facilitate its proper function, without departing from the scope of the scope of the disclosure.

Referring still to FIG. 13, the fluid monitoring and handling system 1200 may further include the EIS fluid analysis system 100, which may be disposed on a skid supported on the drilling platform 1304. The EIS fluid analysis system 100 may, for example, continuously or intermittently measure the electro-rheology of the drilling fluid 1322. As illustrated, the drilling fluid 1322 may be taken from the mud pit 1202 via the mud pit line 1206 and an analyzed drilling fluid may be returned to the mud pit 1202 via the return line 1208. Alternatively, the electro-rheology of the drilling fluid 1322 may be measured, recorded, and/or analyzed at fluid reconditioning system 1222, or at any other suitable location, even while in the wellbore 1318 if desired.

Thus, the fluid monitoring and handling system 1200 may advantageously monitor the concentration of one or more drilling fluid additives using the example method disclosed herein. The fluid monitoring and handling system 1200 may also generate automatic warnings to the personnel when the concentrations deviate from preset safety margins and/or automatically add additional amounts of the one or more drilling fluid additives to the drilling fluid when the concentrations deviate from preset safety margins.

Figure 14:
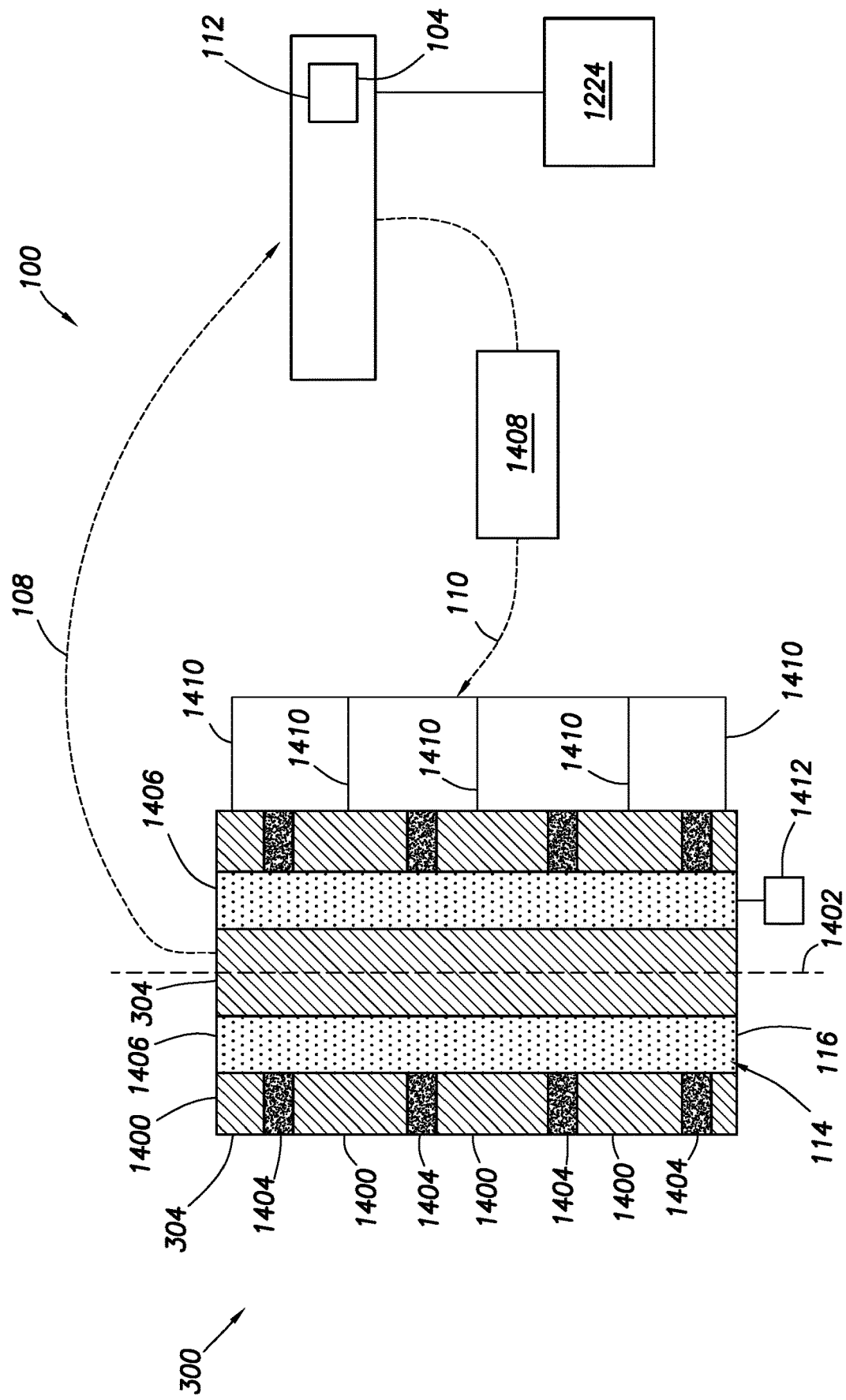
FIG. 14 illustrates an example EIS fluid analysis system.

FIG. 14 illustrates another alternative configuration of EIS fluid analysis system 100. The EIS fluid analysis system 100 shown on FIG. 14 may be incorporated, for example, into fluid monitoring and handling system 1200 to characterize the sag of a drilling fluid at the wellsite. As illustrated, EIS fluid analysis system 100 may be in the form of a concentric cylinder probe 300 that includes an outer cylindrical container 302 and an inner cylinder 304. Outer cylindrical container 302 may be any suitable container for holding a sample fluid 114 that includes particulate additives 116. Inner cylinder 304 nay be disposed in outer cylindrical container 302. Sample fluid 114 is disposed in gap 1406 between outer cylindrical container 302 and inner cylinder 304. Concentric cylinder probe 300 is shown in a vertical configuration. While concentric cylinder probe 300 is shown in the vertical configuration, it should be understood that concentric cylinder probe 300 may disposed in other configurations, including, but not limited to, horizontal and angled configurations. It should be understood that concentric cylinder probe 300 should be considered in a vertical configuration where angle $\phi$ of concentric cylinder probe 300 from horizontal is from 85° to 95°. While concentric cylinder probe 300 is described as being included of cylinders (e.g., outer cylindrical container 302 and an inner cylinder 304), it should be understood that other suitable configurations (may be used and EIS fluid analysis system 100 should not be limited to use of only concentric cylinders.

As illustrated outer cylindrical container 302 may be segmented and include multiple sections 1400. The sections 1400 may be longitudinally spaced. Each of sections 1400 may extend circumferentially around longitudinal axis 1402. Sections 1400 may be separated by insulated spacers 1404. Insulated spacers 1404 may electrically insulations sections 1400 from one another. Insulations sections may include any suitable insulating material, including, but not limited to, polytetrafluoroethylene, ceramic, glass, polyether ether ketone, and other suitable insulators as will be appreciated by those of ordinary skill in the art.

EIS analyzer 104 may be in signal communication with concentric cylinder probe 300. As illustrated, lines 108, 110 may couple inner cylinder 304 and outer cylindrical container 302, respectively, to EIS analyzer 104. EIS analyzer 104 may receive a signal (e.g., alternating current signal) from inner cylinder 304 that traveled across gap 1406. As previously described, gap 1406 may be filled with sample fluid 114. The EIS analyzer 104 may include a signal generator 112. As illustrated, signal generator 112 is shown as a component of EIS analyzer 104, but signal generator 112 may also be separate from EIS analyzer 104. Signal generator 112 by way of EIS analyzer, for example, may apply an electric signal, such as an AC signal, to outer cylindrical container 302 through line 110. EIS fluid analysis system 100 may further include a switching device 1408. Switching device 1408 may selectively excite one or more sections 1400 of outer cylindrical container with the electric signal by way of legs 1410 of line 110. Switching device 1408 may include any suitable type of device for between legs 1410, including, but not limited to, a relay and other suitable switching devices, such as a mechanical or solid state relay, as will be appreciated by those of ordinary skill in the art. Computer system 1224 may be communicatively coupled to EIS analyzer 104, as shown in FIG. 14. Computer system 1224 may model the impedance obtain from EIS analyzer 104 for characterization of the sag of the drilling fluid. Optionally, EIS fluid analysis system 100 may further include a temperature controller 1412. Temperature controller 1412 may include one or more components (none shown separately) to control temperature of sample fluid 114 in concentric cylinder probe 300, for example, to simulate well conditions. By way of example, temperature controller 1412 may include a temperature sensor, such as a thermocouple and/or a heater.

Accordingly, this disclosure describes systems and methods that use EIS for analyzing sag behavior of drilling fluids. Without limitation, the systems and methods may further be characterized by one or more of the following statements:

Statement 1: A method for drilling a wellbore may include circulating a drilling fluid in a wellbore. The method may further include extending the wellbore into one or more subterranean formations. The method may further include measuring impedance of at least a portion of the drilling fluid over time as one or more particulate additives in the drilling fluid settle. The method may further include determining one or more model elements of an equivalent circuit model for modeling frequency responses of the drilling fluid from the impedance. The method may further include determining sag behavior of the drilling fluid based, at least partially, on the one or more model elements.

Statement 2: The method of statement 1, wherein the measuring the impedance of the portion of the drilling fluid may include controlling temperature of the drilling fluid.

Statement 3: The method of statement 1 or statement 2, wherein the measuring the impedance of the portion of the drilling fluid may include placing the portion of the drilling fluid in a container and applying an electric signal to the portion in the container.

Statement 4: The method of statement 3, wherein the electric signal may include an alternating current signal.

Statement 5: The method of statement 3, wherein the container may include a pair of plates arranged that are generally parallel and arranged in a vertical configuration, the electric signal may be received at one of the plates and injected into the portion from another one of the plates.

Statement 6: The method of statement 3, wherein the container may include a pair of plates arranged that are generally parallel and arranged in a horizontal configuration, the electric signal may be received at one of the plates and injected into the portion from another one of the plates.

Statement 7: The method of any preceding statement, wherein the measuring the impedance of the portion of the drilling fluid may include placing the portion in a probe comprising an outer container and an inner container, the portion may be disposed in a gap between the outer container and the inner container.

Statement 8: The method of any preceding statement, wherein the measuring the impedance of the portion of the drilling fluid may include placing the portion in a concentric cylinder probe may include an outer cylindrical container and an inner cylinder, the portion may be disposed in a gap between the outer cylindrical container and the inner cylinder.

Statement 9: The method of statement 8, wherein the measuring may include selectively exciting portions of the outer cylindrical container, wherein the portions may be longitudinally spaced, wherein insulated spacers may separate the portions.

Statement 10: The method of statement 9, wherein the insulated spacers may include polytetrafluoroethylene.

Statement 11: The method of any preceding statement, wherein the equivalent circuit model may include a first capacitor C1, a second capacitor C2, a resistor R1, a first constant phase element CPE1, and a first constant phase element CPE2, and wherein an equivalent circuit impedance ($Z_{eq}$) is given by:

$$Z_{eq}(\omega) = Z_{CPE1}(\omega) + \frac{Z_{R1}Z_{C1}(\omega)(Z_{C2}(\omega) + Z_{CPE2}(\omega))}{Z_{C1}(\omega)(Z_{C2}(\omega) + Z_{CPE2}(\omega)) + Z_{R1}(Z_{C1}(\omega) + Z_{C2}(\omega) + Z_{CPE2}(\omega))}$$

Wherein $Z_{C1}$, $Z_{C2}$, $Z_{R1}$, $Z_{CPE1}$, $Z_{CPE2}$ represent impedances of the first capacitor C1, the second capacitor C2, resistor R1, the first constant phase element CPE1, and the second constant phase element CPE2, respectively.

Statement 12: The method of any preceding statement, wherein the determining sag behavior of the drilling fluid based, at least partially, the one or more model elements may use a correlation between the one or more model elements and sag.

Statement 13: The method of statement 12, further including generating frequency responses for one or more sample fluids having a known composition over time, calculating an equivalent impedance of the equivalent circuit model for modeling the frequency responses, the equivalent circuit model comprising one or more model elements, and generating the correlation between the one or more model elements and sag of the one or more sample fluids over time.

Statement 14: The method of any preceding statement, wherein the one or more particulate additives may include a weighting agent, wherein the portion may be obtained from a mud pit, wherein the measuring the impedance of the portion of the drilling fluid may include placing the portion in a concentric cylinder probe comprising an outer cylindrical container and an inner cylinder, wherein the concentric cylinder probe may be disposed at an angle with respect to horizontal of about 10° to 85°, wherein the sample may be disposed in a gap between the outer cylindrical container and the inner cylinder, and wherein the measuring may include selectively exciting portions of the outer cylindrical container, wherein the portions may longitudinally spaced, wherein insulated spacers may separate the portions.

Statement 15: A drilling system may include a drill string. The drilling system may further comprise a drill bit attached to a distal end of the drill string. The drilling system may further comprise a fluid monitoring and handling system comprising a mud pit operable to receive a drilling fluid from a wellbore. The fluid monitoring and handling system may further include a mud pump operable to circulate the drilling fluid. The fluid monitoring and handling system may further include an electrochemical impedance spectroscopy system. The electrochemical impedance spectroscopy system may include a container for holding a sample of drilling fluid. The electrochemical impedance spectroscopy system may include an electrochemical impedance spectroscopy analyzer for measuring impedance of the sample. The electrochemical impedance spectroscopy system may include a computer system in signal communication with the electrochemical impedance spectroscopy system. The computer system may include a processor and a non-transitory computer readable storage medium that when executed by the processor causes the computer system to determine sag behavior of the sample based, at least partially, on the impedance.

Statement 16: The drilling system of statement 15, wherein non-transitory computer readable storage medium may further cause the computer system to determine one or more model elements of an equivalent circuit model for modeling frequency responses of the drilling fluid from the impedance, the sag behavior being determined based, at least partially, on the one or more model elements.

Statement 17: The drilling system of statement 15 or statement, wherein the container may include a concentric cylinder probe that may include an outer cylindrical container and an inner cylinder, the sample being disposable in a gap between the outer cylindrical container and the inner cylinder.

Statement 18: The drilling system of statement 17, wherein the outer cylindrical container may include sections that are longitudinally spaced and insulated spacers that separate the sections, wherein the electrochemical impedance spectroscopy system may include a switching device to selectively send an alternating current signal from the electrochemical impedance spectroscopy to one or more of the sections.

Statement 19: An electrochemical impedance spectroscopy system may include a concentric sample probe comprising an outer container and an inner portion. A gap may be disposed between the outer container and the inner portion. The outer container may include sections that are longitudinally spaced and insulated spacers disposed between the sections. The electrochemical impedance spectroscopy system may further include an electrochemical impedance spectroscopy analyzer in signal communication with the concentric sample probe, the electrochemical impedance spectroscopy analyzer comprising a signal generator. The electrochemical impedance spectroscopy system may further include a switching device operable to selectively send an excitation signal from the electrochemical impedance spectroscopy analyzer to one or more of the sections of the outer container.

Statement 20: The electrochemical impedance spectroscopy system of statement 19, wherein the outer container may include an outer cylindrical container, and wherein the inner portion may include an inner cylinder.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method for drilling a wellbore comprising:
   circulating a drilling fluid in a wellbore;
   extending the wellbore into one or more subterranean formations;
   measuring impedance of at least a portion of the drilling fluid over time as one or more particulate additives in the drilling fluid settle;
   determining one or more model elements of an equivalent circuit model for modeling frequency responses of the drilling fluid from the impedance; and
   determining sag behavior of the drilling fluid based, at least partially, on the one or more model elements.

2. The method of claim 1, wherein the measuring the impedance of the portion of the drilling fluid comprises controlling temperature of the drilling fluid.

3. The method of claim 1, wherein the measuring the impedance of the portion of the drilling fluid comprises placing the portion in a probe comprising an outer container and an inner container, the portion being disposed in a gap between the outer container and the inner container.

4. The method of claim 1, wherein the equivalent circuit model comprises a first capacitor C1, a second capacitor C2, a resistor R1, a first constant phase element CPE1, and a first constant phase element CPE2, and wherein an equivalent circuit impedance (Zeq) is given by:

$$Z_{eq}(\omega) = Z_{CPE1}(\omega) + \frac{Z_{R1}Z_{C1}(\omega)(Z_{C2}(\omega) + Z_{CPE2}(\omega))}{Z_{C1}(\omega)(Z_{C2}(\omega) + Z_{CPE2}(\omega)) + Z_{R1}(Z_{C1}(\omega) + Z_{C2}(\omega) + Z_{CPE2}(\omega))}$$

Wherein ZC1, ZC2, ZR1, ZCPE1, ZCPE2 represent impedances of the first capacitor C1, the second capacitor C2, resistor R1, the first constant phase element CPE1, and the second constant phase element CPE2, respectively.

5. The method of claim 1, wherein the one or more particulate additives comprise a weighting agent, wherein the portion is obtained from a mud pit, wherein the measuring the impedance of the portion of the drilling fluid comprises placing the portion in a concentric cylinder probe comprising an outer cylindrical container and an inner cylinder, wherein the concentric cylinder probe is disposed at an angle with respect to horizontal of 10° to 85°, wherein the sample is disposed in a gap between the outer cylindrical container and the inner cylinder, and wherein the measuring comprising selectively exciting portions of the outer cylindrical container, wherein the portions are longitudinally spaced, wherein insulated spacers separate the portions.

6. The method of claim 1, wherein the determining sag behavior of the drilling fluid based, at least partially, the one or more model elements uses a correlation between the one or more model elements and sag.

7. The method of claim 6, further comprising generating frequency responses for one or more sample fluids having a known composition over time, calculating an equivalent impedance of the equivalent circuit model for modeling the frequency responses, the equivalent circuit model comprising one or more model elements, and generating the correlation between the one or more model elements and sag of the one or more sample fluids over time.

8. The method of claim 1, wherein the measuring the impedance of the portion of the drilling fluid comprises placing the portion of the drilling fluid in a container and applying an electric signal to the portion in the container.

9. The method of claim 8, wherein the electric signal comprises an alternating current signal.

10. The method of claim 8, wherein the container comprises a pair of plates arranged that are generally parallel and arranged in a vertical configuration, the electric signal being received at one of the plates and injected into the portion from another one of the plates.

11. The method of claim 8, wherein the container comprises a pair of plates arranged that are generally parallel and arranged in a horizontal configuration, the electric signal being received at one of the plates and injected into the portion from another one of the plates.

12. The method of claim 1, wherein the measuring the impedance of the portion of the drilling fluid comprises placing the portion in a concentric cylinder probe comprising an outer cylindrical container and an inner cylinder, the portion being disposed in a gap between the outer cylindrical container and the inner cylinder.

13. The method of claim 12, wherein the measuring comprising selectively exciting portions of the outer cylindrical container, wherein the portions are longitudinally spaced, wherein insulated spacers separate the portions.

14. The method of claim 13, wherein the insulated spacers comprise polytetrafluoroethylene.

15. A drilling system comprising:
a drill string;
a drill bit attached to a distal end of the drill string;
a fluid monitoring and handling system comprising
    a mud pit operable to receive a drilling fluid from a wellbore;
    a mud pump operable to circulate the drilling fluid; and
    an electrochemical impedance spectroscopy system comprising a container for holding a sample of drilling fluid and an electrochemical impedance spectroscopy analyzer for measuring impedance of the sample; and
a computer system in signal communication with the electrochemical impedance spectroscopy system, wherein the computer system comprises a processor and a non-transitory computer readable storage medium that when executed by the processor causes the computer system to determine sag behavior of the sample based, at least partially, on the impedance.

16. The drilling system of claim 15, wherein non-transitory computer readable storage medium further causes the computer system to determine one or more model elements of an equivalent circuit model for modeling frequency responses of the drilling fluid from the impedance, the sag behavior being determined based, at least partially, on the one or more model elements.

17. The drilling system of claim 15, wherein the container comprises a concentric cylinder probe comprising an outer cylindrical container and an inner cylinder, the sample being disposable in a gap between the outer cylindrical container and the inner cylinder.

18. The drilling system of claim 17, wherein the outer cylindrical container comprises sections that are longitudinally spaced and insulated spacers that separate the sections, wherein the electrochemical impedance spectroscopy system comprises a switching device to selectively send an alternating current signal from the electrochemical impedance spectroscopy to one or more of the sections.

19. The drilling system of claim 15, wherein the container comprises a concentric cylinder probe comprising an outer container and an inner portion, wherein a gap is disposed between the outer container and the inner portion, and wherein the outer container comprises sections that are longitudinally spaced and insulated spacers disposed between the sections.

20. The drilling system of claim 19, wherein the outer container comprises an outer cylindrical container, and wherein the inner portion comprises an inner cylinder.

* * * * *